United States Patent
Kautzsch

(10) Patent No.: US 10,031,062 B2
(45) Date of Patent: Jul. 24, 2018

(54) PARTICLE SENSOR AND METHOD FOR SENSING PARTICLES IN A FLUID

(71) Applicant: Infineon Technologies Dresden GmbH, Dresden (DE)

(72) Inventor: Thoralf Kautzsch, Dresden (DE)

(73) Assignee: INFINEON TECHNOLOGIES DRESDEN GMBH, Dresden (DE)

( * ) Notice: Subject to any disclaimer, the term of this patent is extended or adjusted under 35 U.S.C. 154(b) by 77 days.

(21) Appl. No.: 15/177,404

(22) Filed: Jun. 9, 2016

(65) Prior Publication Data

US 2017/0356837 A1 Dec. 14, 2017

(51) Int. Cl.
*G01N 1/10* (2006.01)
*G01N 15/14* (2006.01)

(52) U.S. Cl.
CPC ..... *G01N 15/1425* (2013.01); *G01N 15/1484* (2013.01)

(58) Field of Classification Search
CPC ........ G01N 21/05; G01N 15/12; G01N 15/14; G01N 15/1404; G01N 15/1484; G01N 2015/1486; G01N 2015/1006; G01N 2015/1037
USPC ............................ 356/335–343, 73, 244, 246
See application file for complete search history.

(56) References Cited

U.S. PATENT DOCUMENTS

| | | | | |
|---|---|---|---|---|
| 3,901,602 | A * | 8/1975 | Gravatt, Jr. ............ | G01N 21/21 250/574 |
| 7,641,856 | B2 * | 1/2010 | Padmanabhan .... | G01N 15/1404 356/39 |
| 8,182,767 | B2 * | 5/2012 | Padmanabhan ... | B01L 3/502715 250/304 |
| 2004/0075824 | A1 * | 4/2004 | Belenkii ............... | G01F 1/7044 356/28 |
| 2015/0377786 | A1 * | 12/2015 | Hosoi ....................... | G01J 1/42 250/216 |

OTHER PUBLICATIONS

Chen et al., "Natural Convection in a Vertical Microchannel", Journal of Heat Transfer, vol. 127, Sep. 2005, pp. 1053-1056.
"New Particle Matter—Dust Sensor (PM1 / PM2.5 / PM10)", Retrieved from www.libelium.com/particle-matter-dust-sensor-pm1-pm25-pm10-air-quality-smart-cities/, May 2015, Libelium, 3 pages.
Kochevar, "Basic Guide to Particle Counters and Particle Counting", Retrieved from www.pmeasuring.com/en, Particle Measuring Systems, Particle Measuring Systems, Inc.,2006, 60 pages.

* cited by examiner

*Primary Examiner* — Hoa Pham
(74) *Attorney, Agent, or Firm* — Viering, Jentschura & Partner MBB

(57) ABSTRACT

Various embodiments provide a particle sensor including: a first carrier, the first carrier including at least one heating structure and a light detecting structure, at least one spacer structure disposed over the first carrier, a second carrier disposed over the at least one spacer structure, the second carrier including a light emitting structure, wherein the first carrier, the second carrier and the at least one spacer structure are arranged to provide a channel for a fluid flow, wherein the light emitting structure is configured to emit light into the channel and wherein the light detecting structure is configured to detect light from the channel.

23 Claims, 15 Drawing Sheets

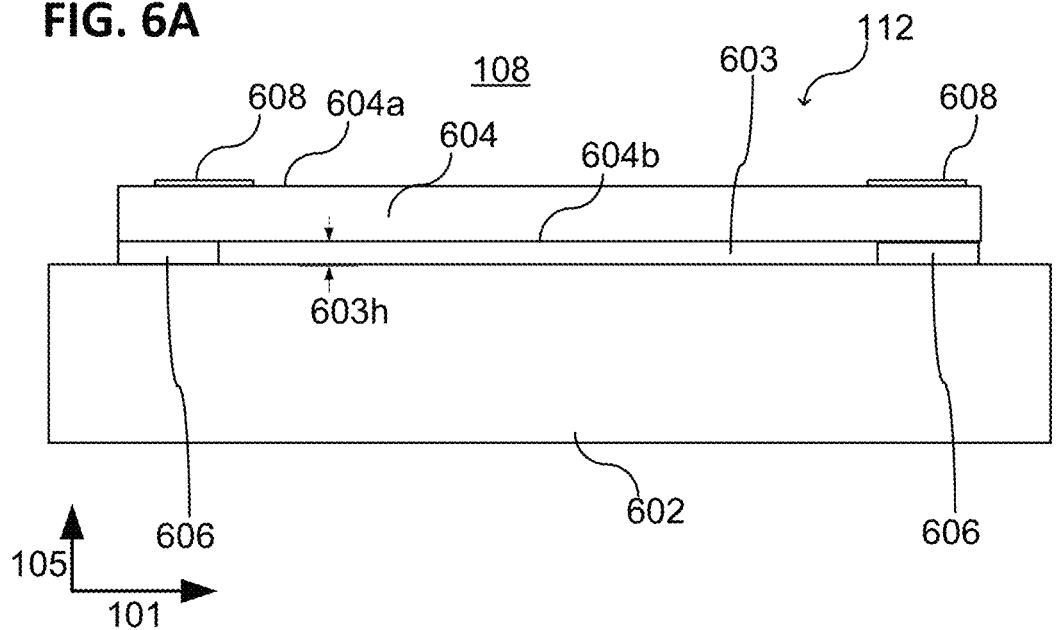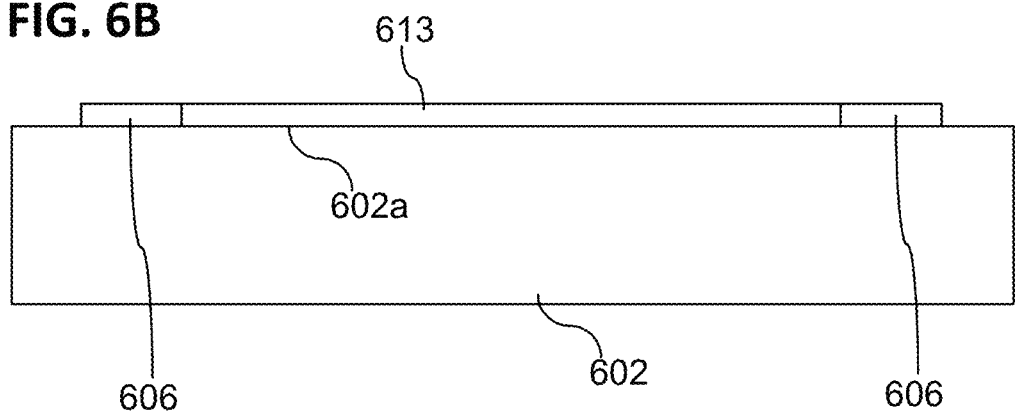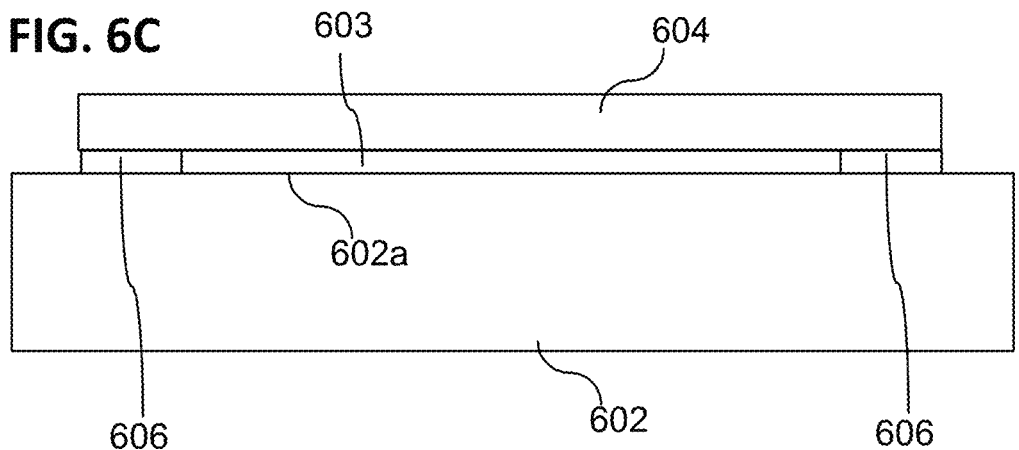

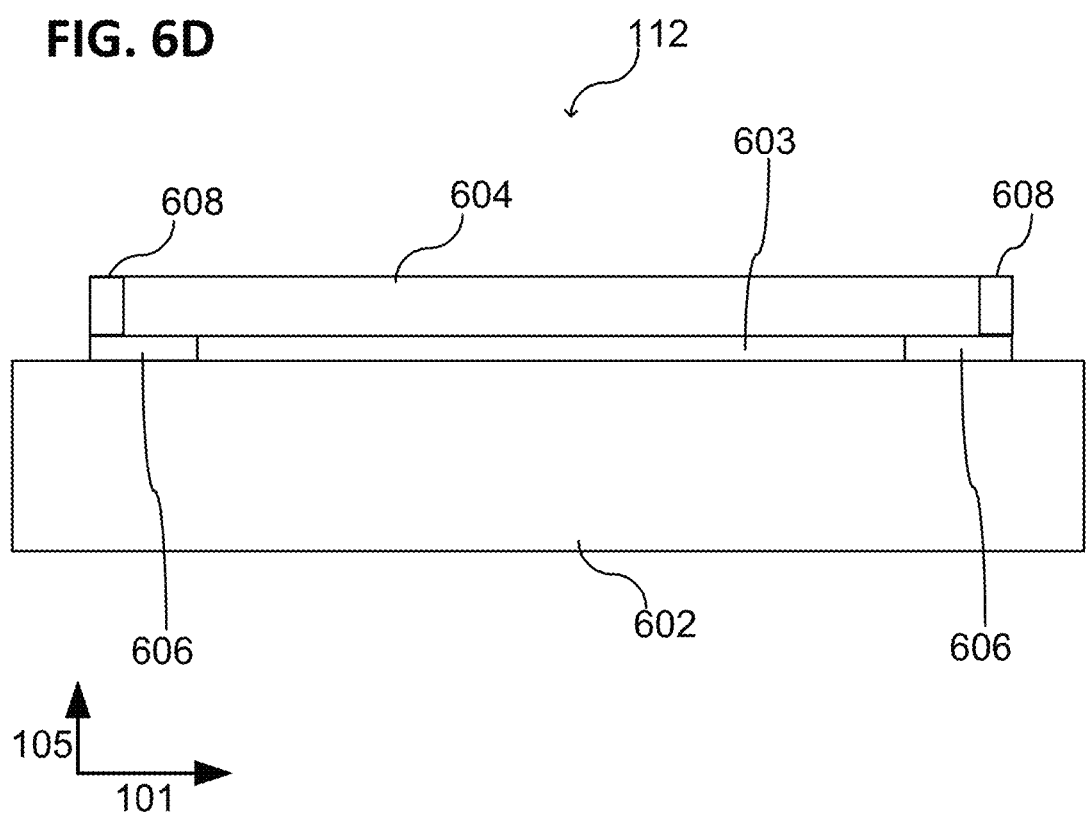

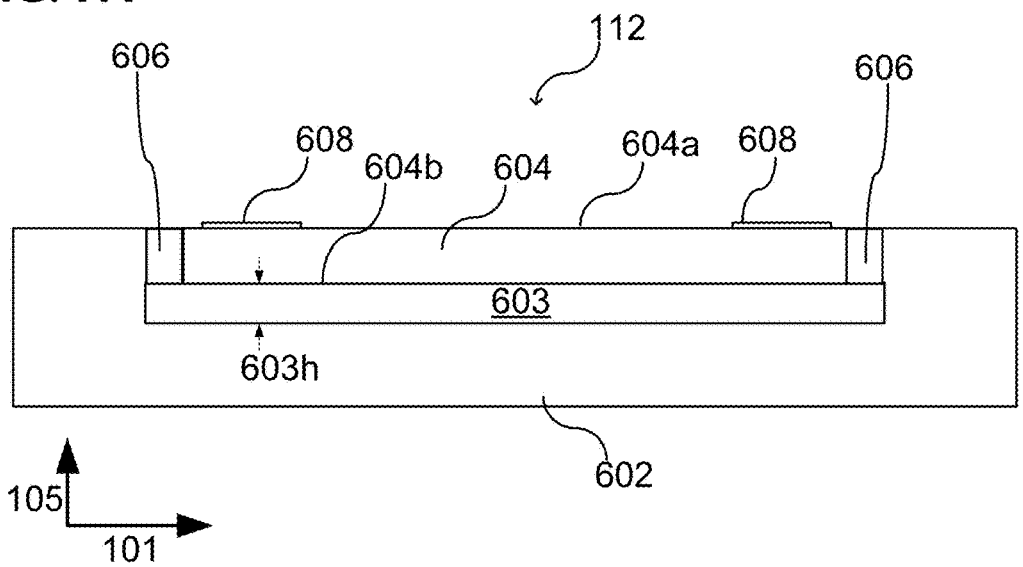
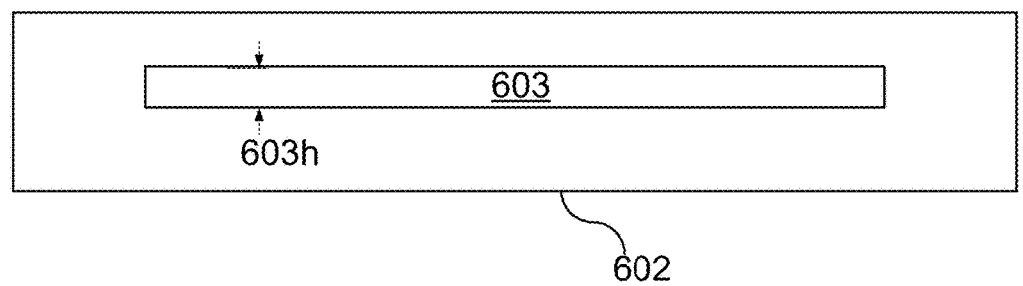
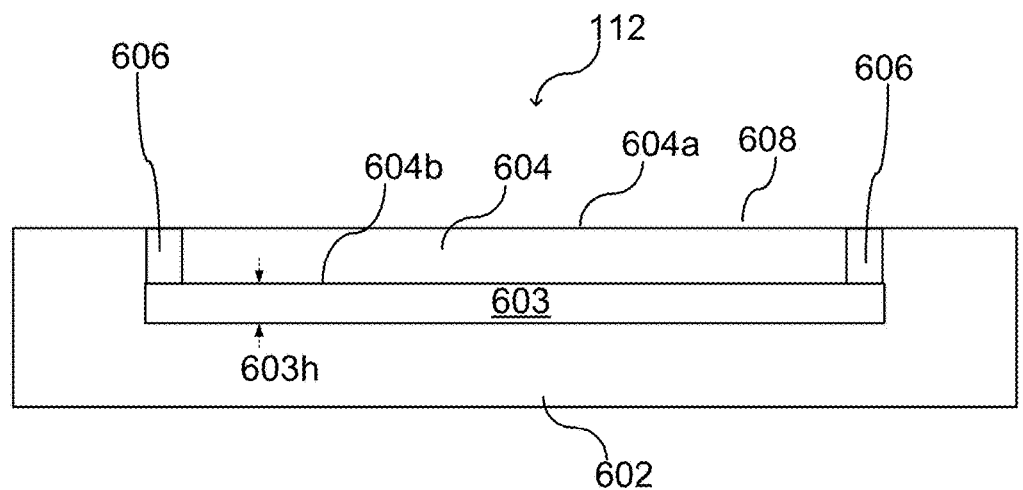

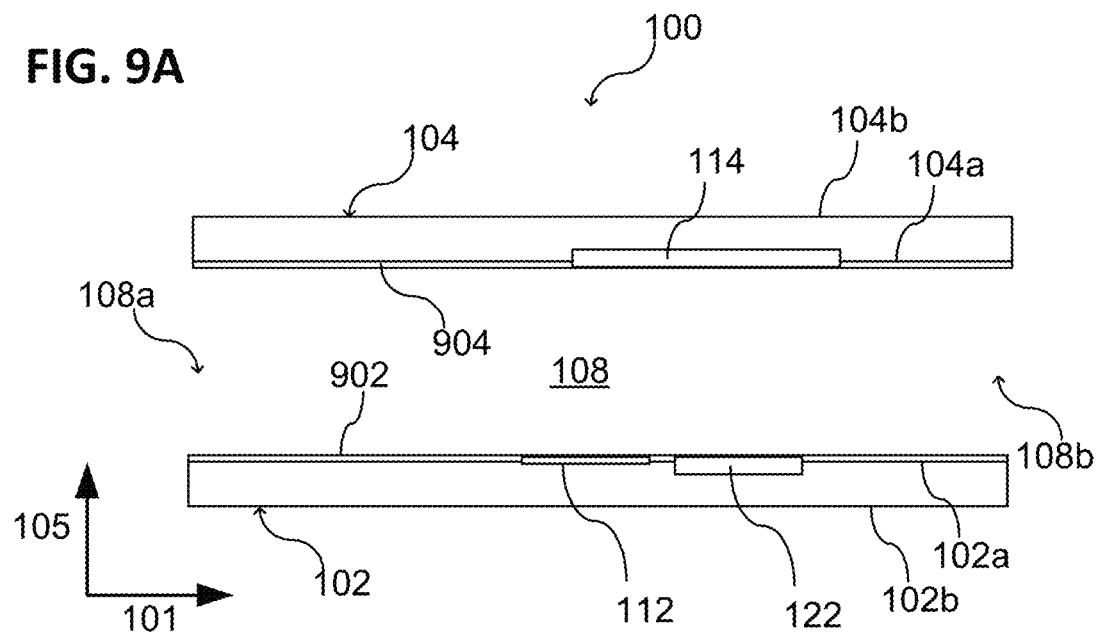
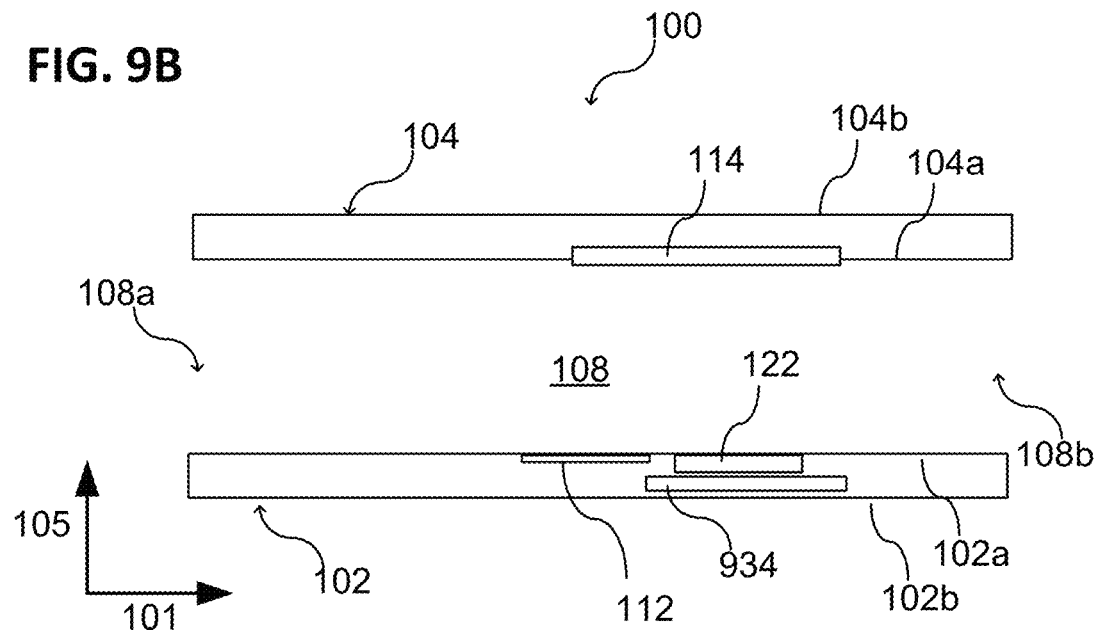

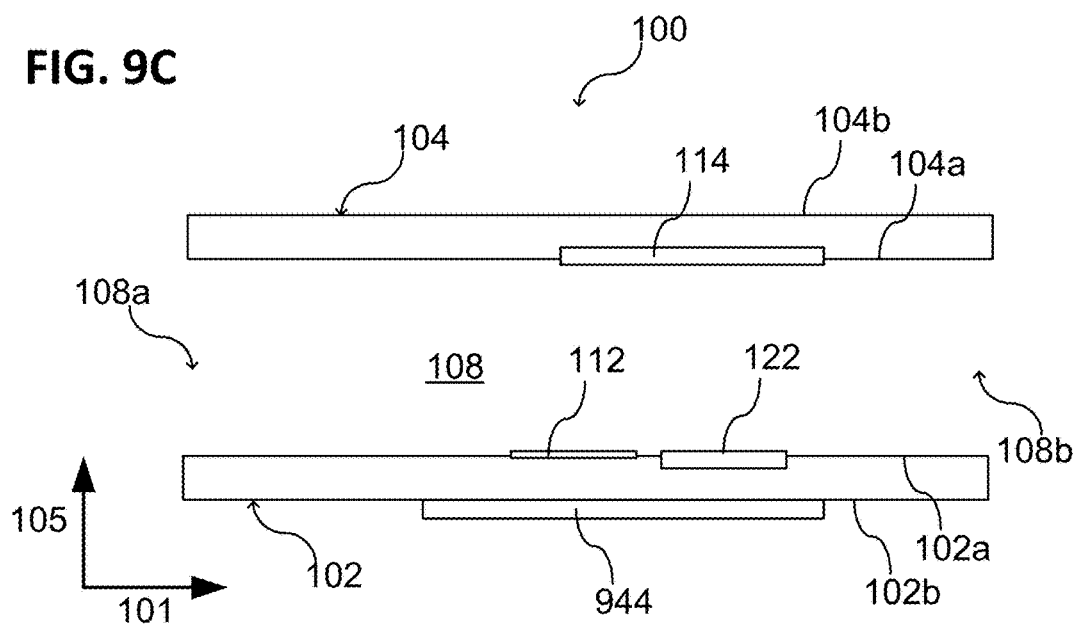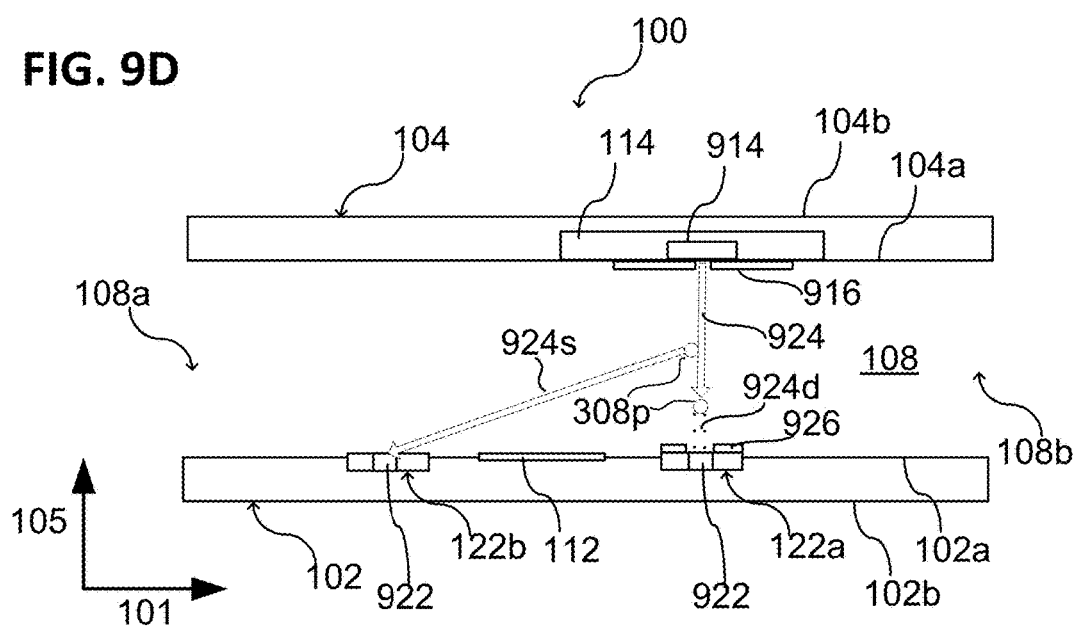

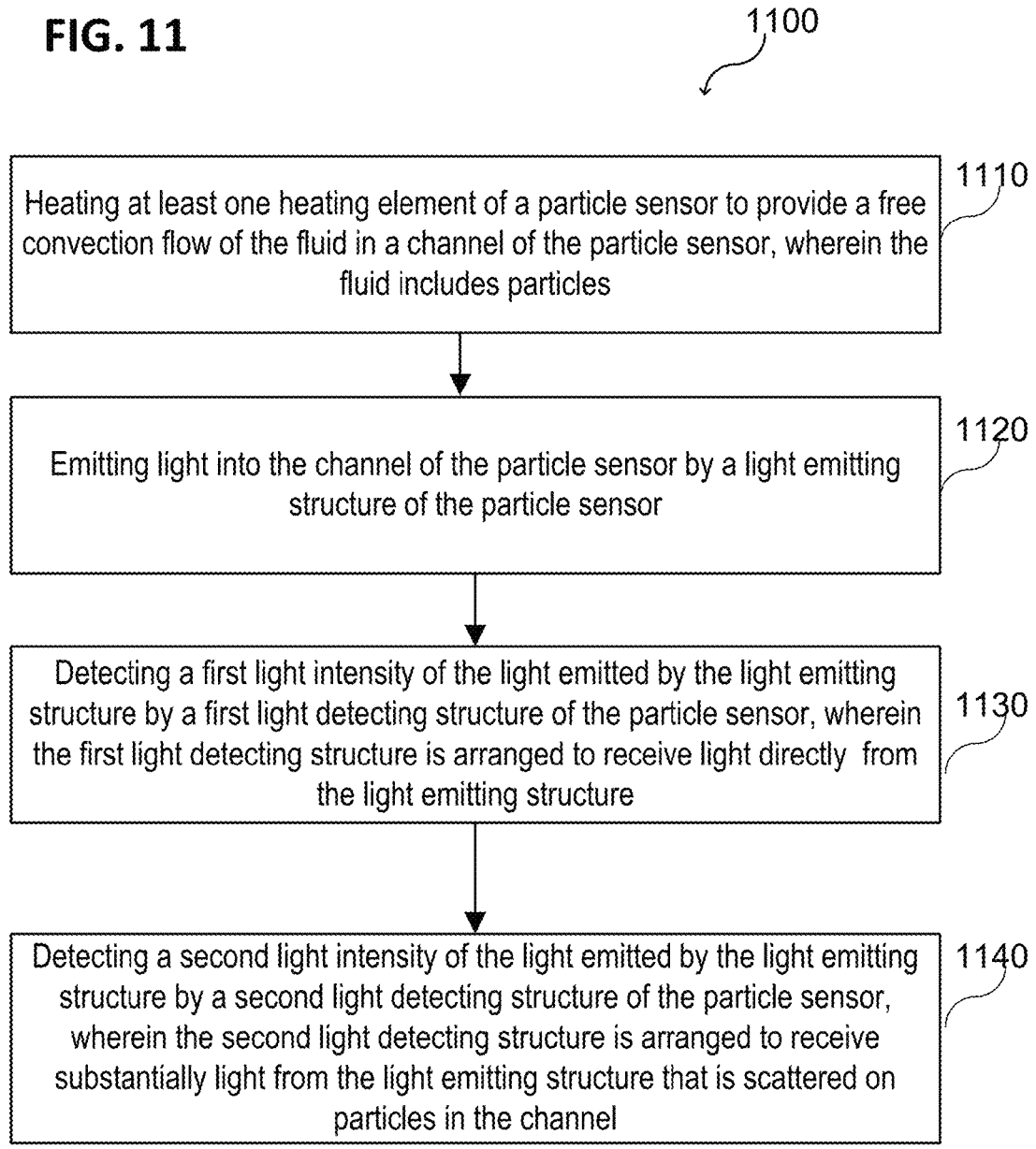

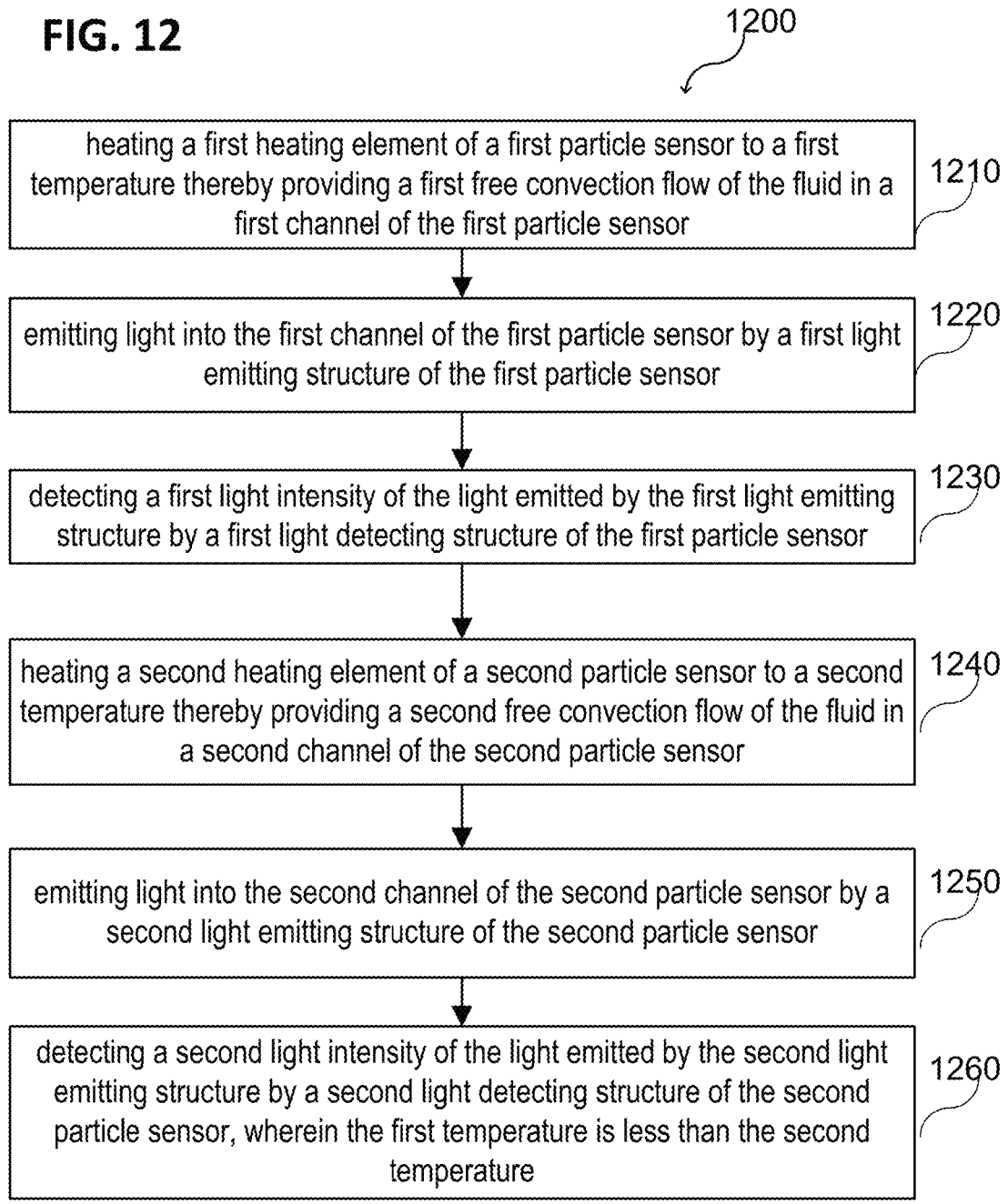

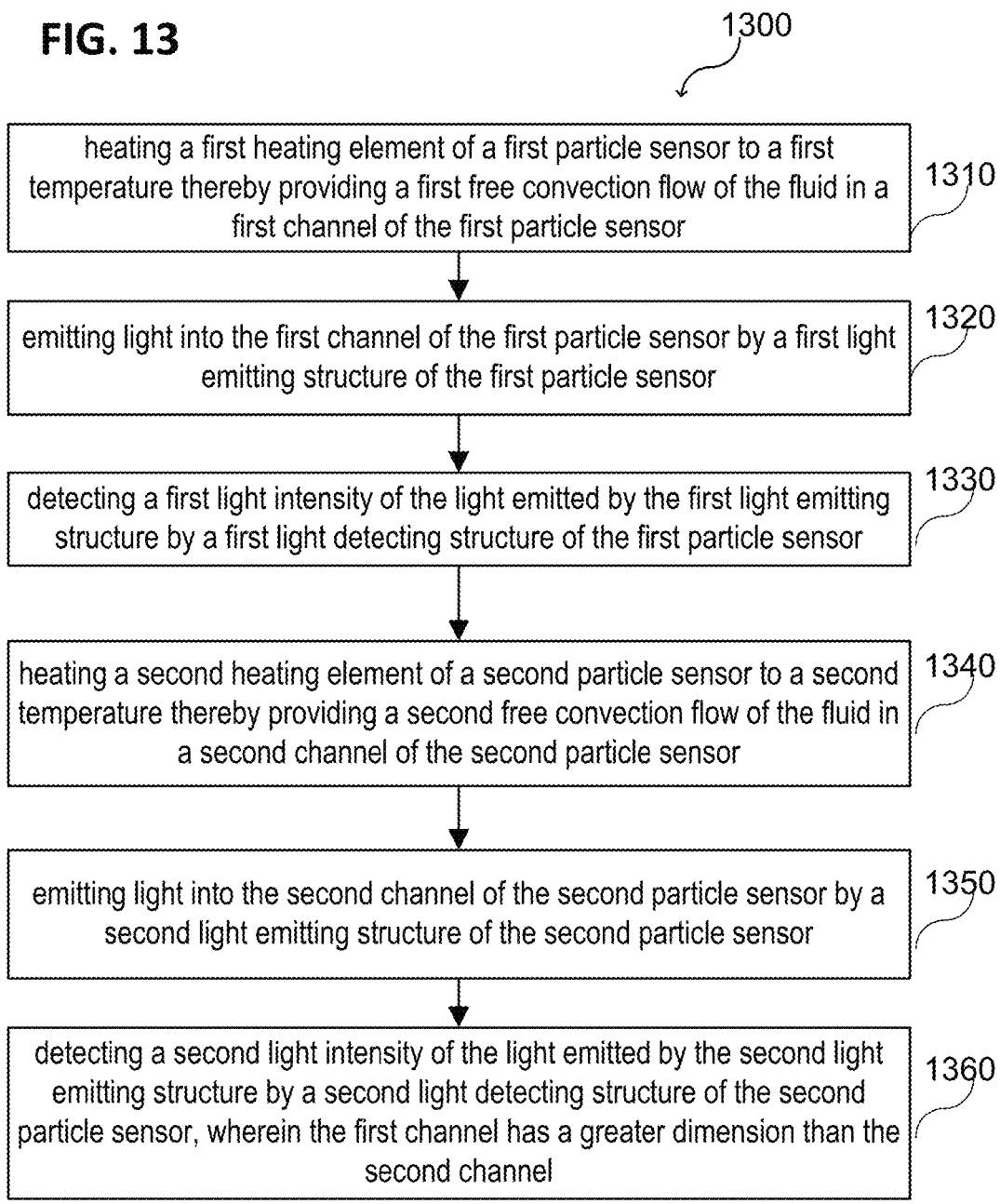

PARTICLE SENSOR AND METHOD FOR SENSING PARTICLES IN A FLUID

TECHNICAL FIELD

Various embodiments relate generally to a particle sensor and a method for sensing particles in a fluid.

BACKGROUND

Particle pollution (also referred to as particulate matter) in the air is a subject that receives more and more attention. Besides monitoring particulate matter in the environment there are predefined requirements regarding particulate matter in clean rooms for processing semiconductor, which makes a monitoring of particulate matter necessary or helpful. Particulate matter may be monitored in gases, e.g. air, or in liquids, e.g. in water for cleanroom processing. Gases and liquids may be referred to as fluids. Particulate matter may include solid and liquid droplets in gases and solid droplets in liquids. The particles may have a wide range of sizes. Particles with a diameter less than 10 micrometers (also referred to as PM10) may be suspected to cause serious health problems. Particles with a diameter less than 2.5 micrometers (also referred to as PM2.5) are referred to as fine particles. Particles with a diameter between 2.5 micrometers and 10 micrometers are referred to as coarse particles. The size of particles may be classified by their statistical mean diameter evaluated, for example, via laser diffraction particle size analysis, condensation particle counter, differential mobility analyzing system, dynamic light scattering, and the like.

SUMMARY

Various embodiments provide a particle sensor including: a first carrier, the first carrier including at least one heating structure and a light detecting structure, at least one spacer structure disposed over the first carrier, a second carrier disposed over the at least one spacer structure, the second carrier including a light emitting structure, wherein the first carrier, the second carrier and the at least one spacer structure are arranged to provide a channel for a fluid flow, wherein the light emitting structure is configured to emit light into the channel and wherein the light detecting structure is configured to detect light from the channel.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIGS. 6A to 6D respectively show a heater structure of a particle sensor in a schematic cross sectional view, according to various embodiments;

FIGS. 7A to 7C respectively show a heater structure of a particle sensor in a schematic cross sectional view, according to various embodiments;

FIGS. 9A to 9D respectively show a particle sensor in a schematic cross sectional view, according to various embodiments;

FIGS. 11 to 13 respectively show a method for sensing particles in a fluid, according to various embodiments.

DESCRIPTION

Figure 1:
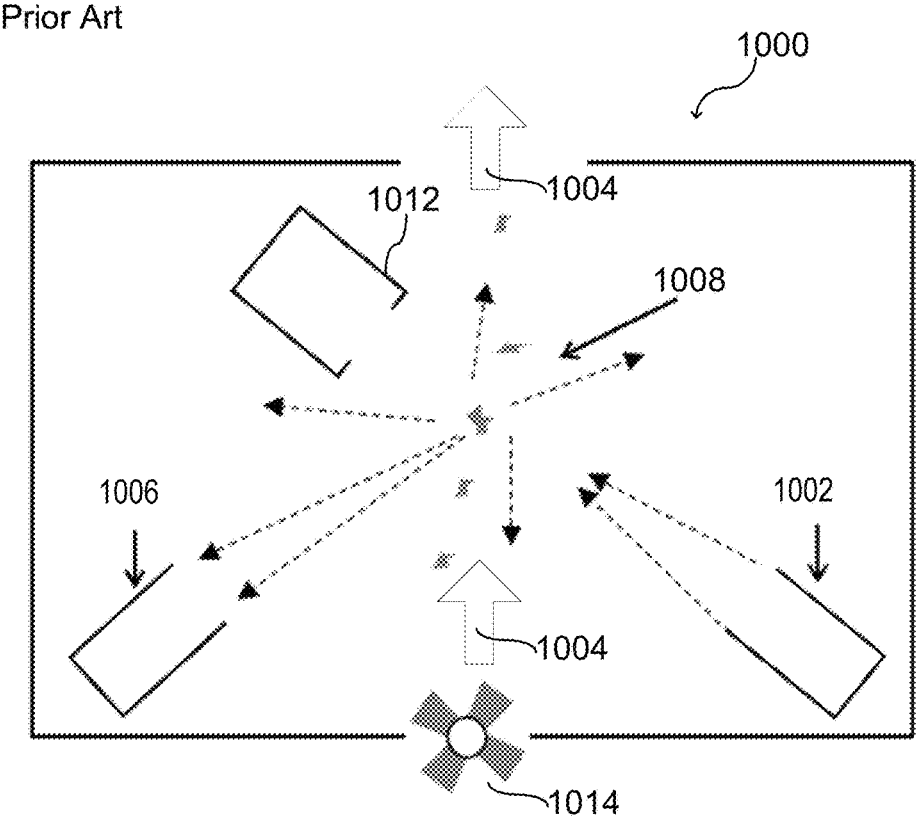
FIG. 1 shows a schematic view of a conventional arrangement for detecting particles.

The following detailed description refers to the accompanying drawings that show, by way of illustration, specific details and embodiments in which the invention may be practiced.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments. Various embodiments are described in connection with methods and various embodiments are described in connection with devices. However, it may be understood that embodiments described in connection with methods may similarly apply to the devices, and vice versa.

The terms "at least one" and "one or more" may be understood to include any integer number greater than or equal to one, i.e. one, two, three, four, [ . . . ], etc. The term "a plurality" may be understood to include any integer number greater than or equal to two, i.e. two, three, four, five, [ . . . ], etc.

The phrase "at least one of [ . . . ] and [ . . . ]" in regard to a group of elements may be used herein to mean at least one element from the group consisting of the elements. For example, the phrase "at least one of [ . . . ] and [ . . . ]" in regard to a group of elements may be used herein to mean a selection of: one of the listed elements, a plurality of one of the listed elements, a plurality of individual listed elements, or a plurality of a multiple of listed elements. The phrase "at least one of [ . . . ] and [ . . . ]" may be used as a logical "and/or".

The word "over", used herein to describe forming a feature, e.g. a layer "over" a side or surface, may be used to mean that the feature, e.g. the layer, may be formed "directly on", e.g. in direct contact with, the implied side or surface. The word "over", used herein to describe forming a feature, e.g. a layer "over" a side or surface, may be used to mean that the feature, e.g. the layer, may be formed "indirectly on"

the implied side or surface with one or more additional layers being arranged between the implied side or surface and the formed layer.

In like manner, the word "cover", used herein to describe a feature disposed over another, e.g. a layer "covering" a side or surface, may be used to mean that the feature, e.g. the layer, may be disposed over, and in direct contact with, the implied side or surface. The word "cover", used herein to describe a feature disposed over another, e.g. a layer "covering" a side or surface, may be used to mean that the feature, e.g. the layer, may be disposed over, and in indirect contact with, the implied side or surface with one or more additional layers being arranged between the implied side or surface and the covering layer.

The term "lateral" used with regards to the "lateral" extension of a structure (or of a structure element) provided on or in a layer (e.g. a substrate, a wafer, or a semiconductor work piece) or "laterally" next to, may be used herein to mean an extension or a positional relationship along a surface of the layer. That means that a surface of a layer (e.g. a surface of a substrate, a surface of a wafer, or a surface of a work piece) may serve as reference, commonly referred to as the main processing surface. Further, the term "width" used with regards to a "width" of a structure (or of a structure element) may be used herein to mean the lateral extension of a structure. Further, the term "height" used with regards to a height of a structure (or of a structure element), may be used herein to mean an extension of a structure along a direction perpendicular to the surface of a layer (e.g. perpendicular to the main processing surface of a layer). The term "thickness" used with regards to a "thickness" of a layer may be used herein to mean the spatial extension of the layer perpendicular to the surface of the support (the material or material structure) on which the layer is deposited. If a surface of the support is parallel to the surface of the layer (e.g. parallel to the main processing surface) the "thickness" of the layer deposited on the surface of the support may be the same as the height of the layer.

The term "coupled" is used herein to mean electrically connected, which may include a direct connection or an indirect connection, wherein an indirect connection may only include additional structures in the current path that not influence the substantial functioning of the described circuit or device. The term "electrically conductively connected" that is used herein to describe an electrical connection between two terminals, two contacts, etc. may be understood as an electrically conductive connection with ohmic behavior, e.g. provided by a metal or degenerate semiconductor in absence of p-n junctions in the current path. The term "contacted" that is used herein to describe an electrical contact between a terminal and a semiconductor region, or the like, may be understood as direct physical and/or direct electrical contact.

The term integrated used with regards to an integrated structure, e.g. an integrated heating structure, an integrated light detecting structure, an integrated light emitting structure, and the like, may be used herein to mean that the structure may be formed in a carrier or layer, at a surface of a carrier or layer, or both over and in a carrier or layer.

The specific thermal conductivity may be referred to as the property of a material to conduct heat. The actual thermal conductivity of a structure may depend on the material and, in non-ideal case, further on other characteristics, as for example, the microstructure of the material. A thermally insulating structure or a thermally insulating material, as described herein, may have a thermal conductivity of less than about 5 W/(K·m) at a temperature of about 20° C.

Examples for thermally insulating materials may be oxides, e.g. metal oxides or half metal oxides, e.g. silicon oxide ($SiO_2$). Further, thermally insulating materials may include porous materials, e.g. with a porosity (i.e. a fraction of the volume of voids over the total volume) less than about 95%, since porous materials may have a reduced thermal conductivity compared to the same non-porous (i.e. dense or bulk) material.

According to various embodiments, a semiconductor layer (e.g. a semiconductor substrate, a semiconductor wafer, a deposited semiconductor layer, an epitaxial semiconductor layer, and the like) may be made of or may include silicon. However, other semiconductor materials of various types may be used in a similar way, e.g. germanium, Group III to V (e.g. SiC), or other types, including for example polymers. In an embodiment, the semiconductor layer is a wafer made of silicon (e.g. p-type doped or n-type doped). In an alternative embodiment, the semiconductor layer is a silicon on insulator (SOI) wafer. According to various embodiments, a carrier may include a single layer or a layer stack of various layers.

Conventionally, there are multiple ways of particle detection and measurement. Particles can be detected by micromechanical systems measuring the change of a physical parameter (e.g. a shift of a resonance frequency of a micromechanical system) caused by settled particles on a micro beam or another suited configuration. However, most common particle sensors use optoelectronic evaluation of light intensity that passed through a test volume.

FIG. 1 shows a schematic view of a commonly used optical particle counter 1000. The optical particle counter 1000 may have a high-intensity light source 1002 (e.g. a laser or a light emitting diode), a controlled air flow 1004 (referred to as viewing volume), and a highly sensitive light gathering detector 1006 (e.g. a photodetector). The controlled air flow 1004 includes particles 1008 to be counted and may be generated by a fan 1014. The particles 1008 may reflect light emitted by the high-intensity light source 1002 into the direction of the light gathering detector 1006. The unscattered light emitted by the high-intensity light source 1002 may be trapped in a light trap 1012.

For a correct quantification of a particle concentration, the air volume under test has to be controlled. This is conventionally done by using the fan 1014 to produce a predefined air flow through the measurement system. Alternatively, the predefined air flow may be provided by means of free convection caused by a heat source.

Conventional sensors may have a size of a few tens or one hundred cubic centimeters. Their operation may be improved by peripheral elements, such as heaters for air drying, a cyclone separator for pre-sorting of particles, and the like.

Figure 2A:
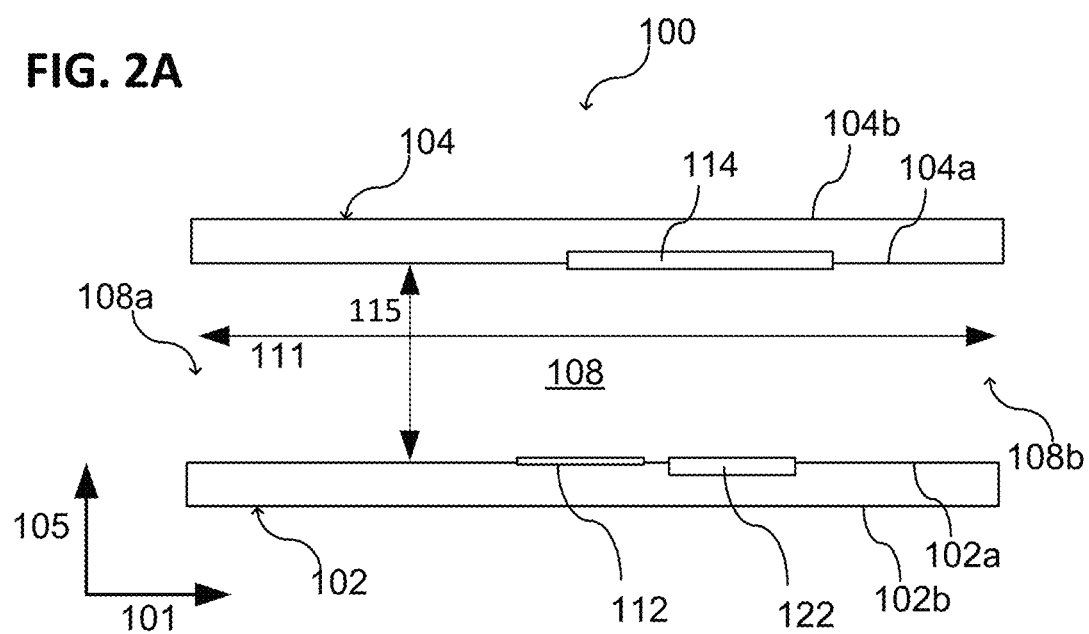
FIGS. 2A and 2B schematically show a particle sensor in different views, according to various embodiments.
Figure 2B:
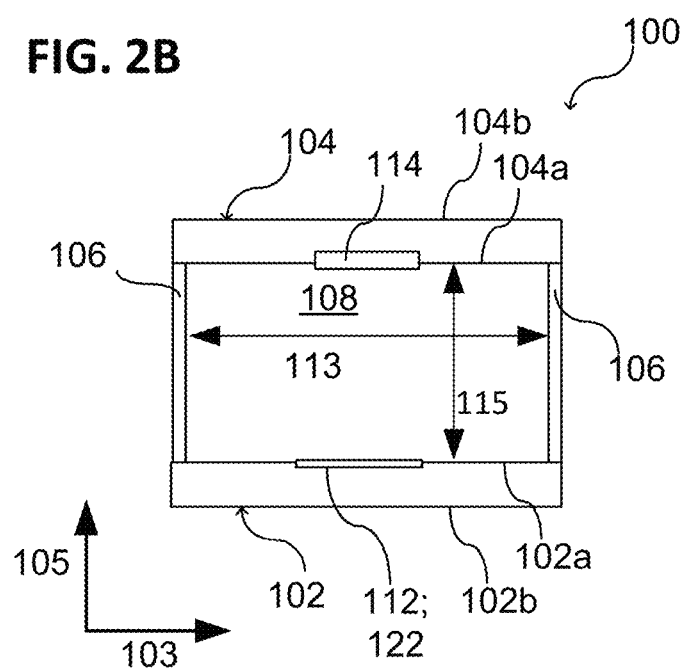

Various embodiments provide a sensor 100, e.g. a particle sensor 100 (also referred to as particle counter 100) that is manufactured in semiconductor technology, as schematically illustrated in FIG. 2A and FIG. 2B in different cross sectional views. The particle sensor 100 may include a first carrier 102. The first carrier 102 may be any type of carrier processable in semiconductor technology, e.g. a semiconductor carrier, e.g. a silicon wafer. The first carrier may include at least one heating structure 112 and at least one light detecting structure 122. The light detecting structure 122 may include at least one light detecting element, e.g. a photo diode. According to various embodiments, the light detecting element may be formed in semiconductor technology integrated in and/or over the first carrier 102. The light detecting structure 122 may include components to measure a light intensity via the at least one light detecting element. The light detecting structure 122 may include a wiring, a measurement circuit, one or more micro-optical elements, and the like.

According to various embodiments, the heating structure 112 may include at least one heating element. According to various embodiments, the heating structure 112 or at least the at least one heating element of the heating structure 112 may be formed in semiconductor technology integrated in and/or over the first carrier 102.

The particle sensor 100 may further include at least one spacer structure 106 disposed over the first carrier 102. The spacer structure 106 may include at least two sidewalls, see FIG. 2B, extending away from the first carrier 102.

The particle sensor 100 may further include a second carrier 104 disposed over the at least one spacer structure 106. The second carrier 104 may include at least one light emitting structure 114. The light emitting structure 114 may include at least one light emitting element, e.g. a light emitting diode, an organic light emitting diode, or a laser diode. According to various embodiments, the light emitting structure 114 or the at least one light emitting element of the light emitting structure 114 may be formed in semiconductor technology integrated in and/or over the second carrier 104. The light emitting structure 114 may include components to emit light with. The light emitting structure 122 may include a wiring, a driver circuit, one or more micro-optical elements, and the like.

According to various embodiments, the first carrier 102, the second carrier 104, and the at least one spacer structure 106 may be arranged to provide a channel 108 for a fluid flow. Illustratively, the first carrier 102, the second carrier 104, and the at least one spacer structure 106 may form a channel 108 in such a way that a fluid, e.g. a gas or a liquid, can flow within the channel 108 into a predefined direction 101.

The heating structure 112 may be configured to substantially heat a fluid that is located in the channel 108, e.g. the heating structure 112 may be arranged at a first surface 102a of the first carrier 102. The light emitting structure 114 may be configured to substantially emit light into the channel 108, e.g. light emitting structure 114 or at least one light emitting element of the light emitting structure 114 may be arranged at a first surface 104a of the second carrier 104. The light detecting structure 122 may be configured to substantially detect light from the channel 108 that is emitted from the light emitting structure 114, e.g. the light detecting structure 122 or at least one light detecting element of the light detecting structure 122 may be arranged at the first surface 102a of the first carrier 102. The first surface 102a of the first carrier 102 may face the first surface 104a of the second carrier 104. The at least two sidewalls of the spacer structure 106 may extend from the first carrier 102 to the second carrier 104, or in other words, each sidewall of the spacer structure 106 may extend from the first surface 102a of the first carrier 102 to the first surface 104a of the second carrier 104.

According to various embodiments, the channel 108 may have at least two openings 108a, 108b defining a flow direction 101 for a fluid from one of the at least two openings 108a, 108b to another one of the at least two openings 108a, 108b.

According to various embodiments, the channel 108 may have an extension into at least one direction that is in the micrometer range; therefore, the channel 108 may be referred to as micro-channel. Further, the channel 108 may have a length 111 along the flow direction 101 in the range from about 1 mm to about 10 mm. Further, the channel 108 may have a width 113 perpendicular to the flow direction in the range from about 0.5 mm to about 2 mm. Further, the channel 108 may have a height 115 perpendicular to the flow direction 101 (and also perpendicular to the width direction 103) in the micrometer range, e.g. in the range from about 10 µm to about 500 µm.

The height 115 of the channel 108 may be defined by the spacer structure 106. The spacer structure 106 may include any type of carrier or patterned layer structure that provides a sufficient height 115. The at least two sidewalls of the spacer structure 106 may be formed of glass, a metal, a polymer, or any other type of material that allows the formation of a sidewall.

The surfaces 102a, 102b, 104a, 104b of the first and second carrier 102, 104 may be so called main processing surfaces of a semiconductor substrate, e.g. of a semiconductor wafer. At least one of the surfaces 102a, 104a may define a lateral direction 101, 103. Referring to this, the heating structure 112 may be arranged laterally next to the light detecting structure 122 or laterally next to at least one light detecting element of the light detecting structure 122.

Various modifications and/or configurations of the particle sensor 100 and details referring to the at least one heating structure 112, the at least one light detecting structure 122, and the at least one light emitting structure 122 are described in the following, wherein the features and/or functionalities described before may be included analogously. Further, the features and/or functionalities described in the following may be included in the particle sensor 100 or may be combined with the particle sensor 100, as described referring to FIGS. 2A to 2B.

Figure 3:
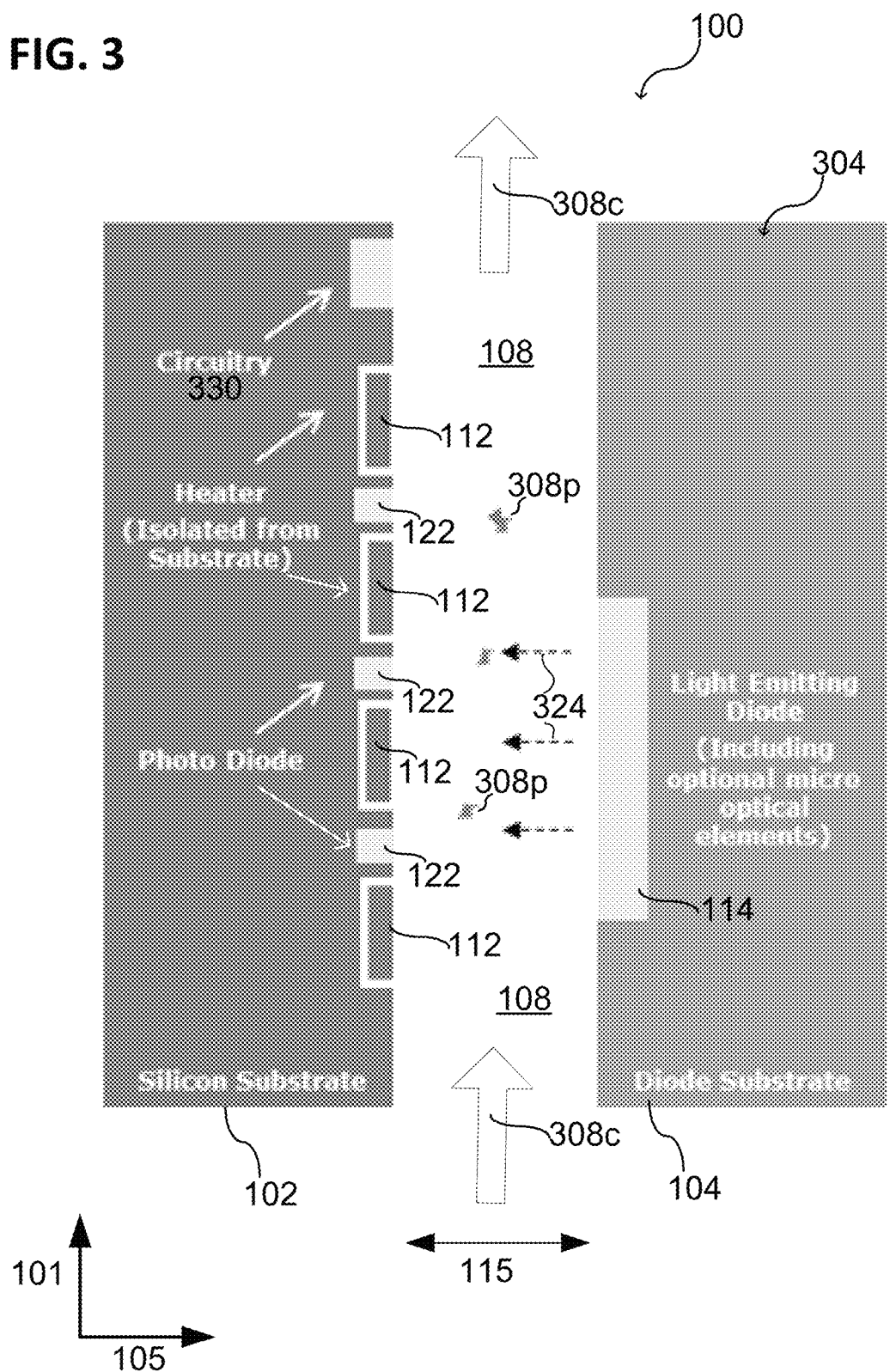
FIG. 3 shows a particle sensor in a schematic cross sectional view, according to various embodiments.

FIG. 3 illustrates a particle sensor 100 in a cross sectional view, according to various embodiments. The particle sensor 100 may include first carrier 102, e.g. a chip. The particle sensor 100 may further include a sequence of light detecting structures 122, e.g. each light detecting structure 122 including at least one on-chip photodiode, and heating structures 112 disposed over and/or in the first carrier 102 in a combination. Using one or more heating structures 112; a controlled free convection 308c may be established in the micro-channel 108 close to the first surface 102a of the first carrier 102. One or more light emitting structures 114, e.g. including at least one light emitting diode, may be disposed opposite to the first carrier 102 and face to face to its surface 102a to illuminate 324 a volume (i.e. a viewing volume to determine a particle concentration) in the micro-channel 108 in between the one or more light emitting structures 114 and at least some of the light detecting structures 122. According to various embodiments, one or more first light detecting structures 122 may be used to directly measure the shading caused by particles 308p moving through the channel 108. Further, e.g. simultaneously, one or more further light detecting structures 122 may be used to measure stray light reflected by particles 308p. Therefore, the one or more light emitting structures 114 may be configured to substantially emit light 324 perpendicular to the flow direction or in other words parallel to the height direction 105 of the particle sensor 100. Using micro-optical elements, as for example, one or more lenses, one or more apertures, one or more mirrors, and the like, may support the configuration of the particle sensor 100 to detect substantially stray light by another one of the light detecting structures than a shadowing of the direct light 324. In other words, the shading caused by the particles 308p located between the respective light emitting structure 114 and the light detecting structure may be detected. This may allow both to count light-colored particles 308*p* by detecting stray light and dark-colored particles 308*p* by detecting the shadowing of the direct light 324.

The channel height 115 and width 113 are defined by the spacer material 106 that is placed on top of the first carrier 102, as described before (see also FIGS. 2A and 2B). The spacer material 106 may be in direct contact to a light emitting unit 304, wherein the light emitting unit 304 may be provided by the second carrier 104 and at least one light emitting structure 114 disposed in and/or over the second carrier 104, as described before.

According to various embodiments, the particle sensor may include a circuit 330 integrated into the first carrier 102, e.g. into the chip. The circuit 330 may include a driver circuit coupled to the one or more heating structures 112. The driver circuit may be configured to control a heating current that flows through the respective heating structure 112. The driver circuit may include a control loop to control the heating current in such a way, that a fluid flow 308*c* is provided in the channel 108 with a flow velocity in the range from about 0.5 mm/s to about 5 mm/s.

According to various embodiments, a plurality of photo diodes may be alternately arranged between the respective heaters, as illustrated in FIG. 3. Each of the photo diodes may have a size of a few hundred to a few thousand square micrometers. The photo diodes may be designed as pinned photo diodes or as diodes with a surface emitter region. According to various embodiments, the photo diodes may be provided in such a way, that their dark current is less than about one pico-ampere.

According to various embodiments, the respective photo diode may have an antireflective coating (e.g. a single layer coating). According to various embodiments, the heating structures 122 may have an antireflective coating (e.g. a single layer coating). The antireflective coating may include or may be a nitride liner. The nitride liner may have a thickness that is adjusted to the wave length of the light emitted by the light emitting structure, e.g. by the light emitting diodes. In doing so, the reflectance of the respective surfaces may be attenuated to about 1%.

According to various embodiments, the light emitting structure 114 (also referred to as a light source) may include at least one light emitting diode or at least one laser diode. The light emitting structure 114 may be configured to illuminate the interior of the channel 108. The light emitting structure 114 may be or may include a Lambertian light source or small-angle emitter, e.g. with an aperture angle of less than about ±20°. According to various embodiments, an aperture structure may be disposed over the light source so that the emitted light illuminates only the photo diodes. Therefore, the aperture structure may have only small slot openings that transmit light into the desired regions of the channel, see FIG. 9D.

The light emitting structure 114 may be positioned on the second carrier 104, wherein the second carrier is a sealing for the micro-channel 108. The second carrier may include optical elements (e.g. micro lenses, aperture, and the like).

The arrangement described herein gives several beneficial opportunities for dust sensing. On one hand, the air flow 308*c* is established by passive heating in a micro channel 108. In this way, the achievable power consumption in operation drops to a few milliwatts—mainly dominated by the current supplied to the light emitting structure 114. The cascade of photo diodes combined with an appropriate algorithm may allow the measurement of a transit time of particles. Therefore, the particle sensor 100 described herein has the capability of self-monitoring. Furthermore, when micro optical elements (shading elements, light traps, and the like) are included in the particle sensor 100, direct measurement of light attenuation by particles and evaluation of scattered light provides a source of additional information about the particle's color, size, and/or shape.

Figure 4:
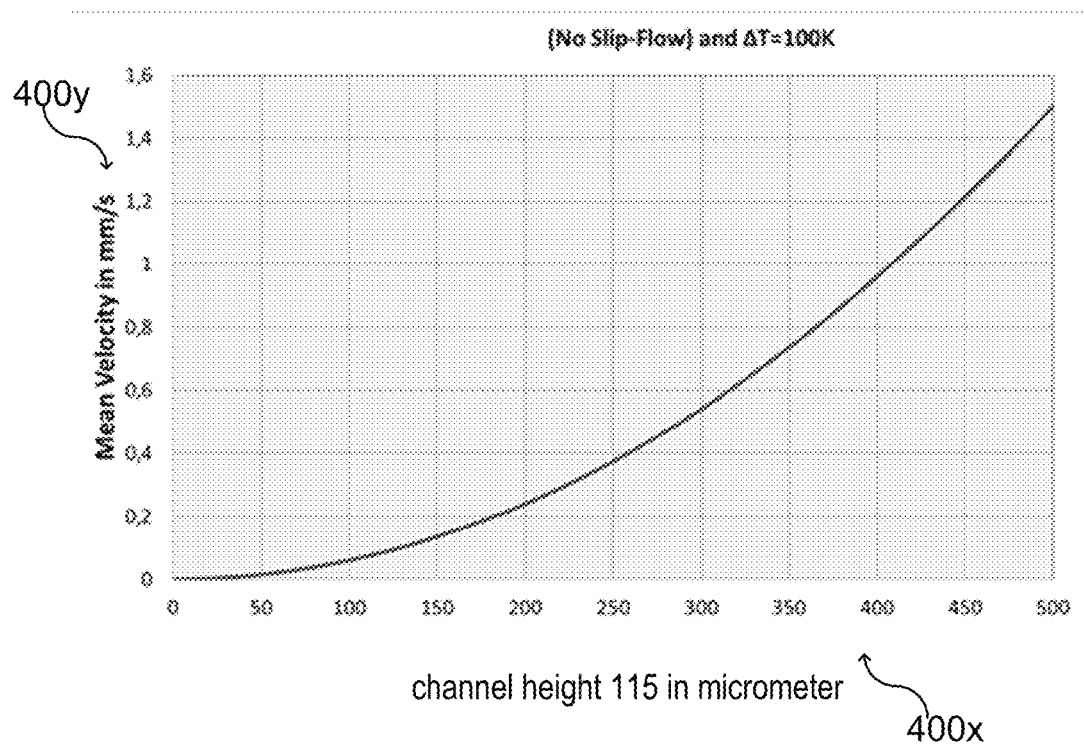
FIG. 4 illustrates a correlation of the mean flow velocity and the channel dimension of a micro-channel of a particle sensor, according to various embodiments.

FIG. 4 illustrates an example of a correlation between the channel dimensions 400*x*, e.g. the height 115, of the channel 108, and the flow velocity 400*y* of the fluid (e.g. a gas, e.g. air) in the channel 108 at a predefined temperature difference, ΔT, of about 100 K between the heating structures 112 of the first carrier 102 and the surrounding, e.g. the second carrier 104. Due to the temperature difference caused by the one or more heating structures 112 a free convection flow 308*c* is caused in the channel 108 with the respective flow velocity. The dimension, e.g. the height 115, of the channel 108 may be selected within an appropriate range to generate a flow velocity in the range from about 0.5 mm/s to about 5 mm/s. The respective flow velocity may allow a selection of particles entering the channel 108 dependent on the diameter of the particles. To allow substantially only particles with a diameter of less than about 10 μm (PM10) entering the channel 108 a flow velocity of less than about 5 mm/s may be provided.

If the dimension of the respective channel 108 is fixed, the control of the temperature difference, i.e. the control of the at least one heating structure 112, may allow controlling the flow velocity 400*y* in the channel 108; and, therefore, a particle selection with respect to the diameter of the particles.

According to various embodiments, the micro-channel 108 may be extended in a millimeter range at directions tangential to the surface 102*a* of the first carrier 102 (e.g. one to ten millimeters in the flow direction 101) and a half micrometer to two millimeters perpendicular to the flow direction 101 along the width direction 103.

A crucial parameter may be the channel height 115. Since free convection may be highly susceptible to the dimensions of the channel 108, the height 115 has to be adjusted to establish a target flow velocity at a given temperature difference. The height 115 of the channel 108 may be provided in the range from a few tens to a few hundred micrometers. At very small Knudsen Numbers (Kn=λ/h, Kn—Knudsen Number, λ—mean free path in air, about 50 nm, h—cavity height), the Navier-Stokes Equation can be strongly simplified if hydro-dynamically fully developed conditions are assumed. With these conditions, the flow velocity 400*y* for free convection is shown in FIG. 4.

The described range of the flow velocity, e.g. in the range from about 0.5 mm/s to about 5 mm/s may be suited for airborne particle sensing, since it covers the option of a size selective inlet. At the cut-point diameter of a particle, the gravitational force is balanced by the upward viscous drag force caused by air flow 308*c* through the vertical channel 108 (see FIG. 3). Smaller diameter particles are accelerated into the channel, while those with terminal settling velocities greater than the sample velocity are rejected. According to various embodiments, the channel 108 may be arranged vertically or with a predefined deviation (e.g. in the range from about 1° to about 70°) from a vertical arrangement.

According to various embodiments, the one or more heating structures may be fabricated by means of a silicon-on-nothing technology or any other suited process such as, for example, a sacrificial layer technology, see FIGS. 6A to 8C. A large cavity underneath the respective heating structure and a sideways fixation, e.g. substantially made of silicon oxide, or any other suitable thermally insulating material, provides a thermal decoupling of the heating structures from the first carrier, e.g. from a silicon substrate. Although, heat radiation may be a strong function of temperature (e.g. described by the Stefan-Boltzmann Law), heat conductance is the dominating effect in the configuration described herein. As an example, at a cavity height of about one micrometer, and an internal pressure of about 20 Pascal (e.g. the processing pressure of suited PECVD depositions), the heat conductance is reduced by a factor of about 500 compared to heat conductance in air under normal pressure of about 1 bar.

Figure 5:
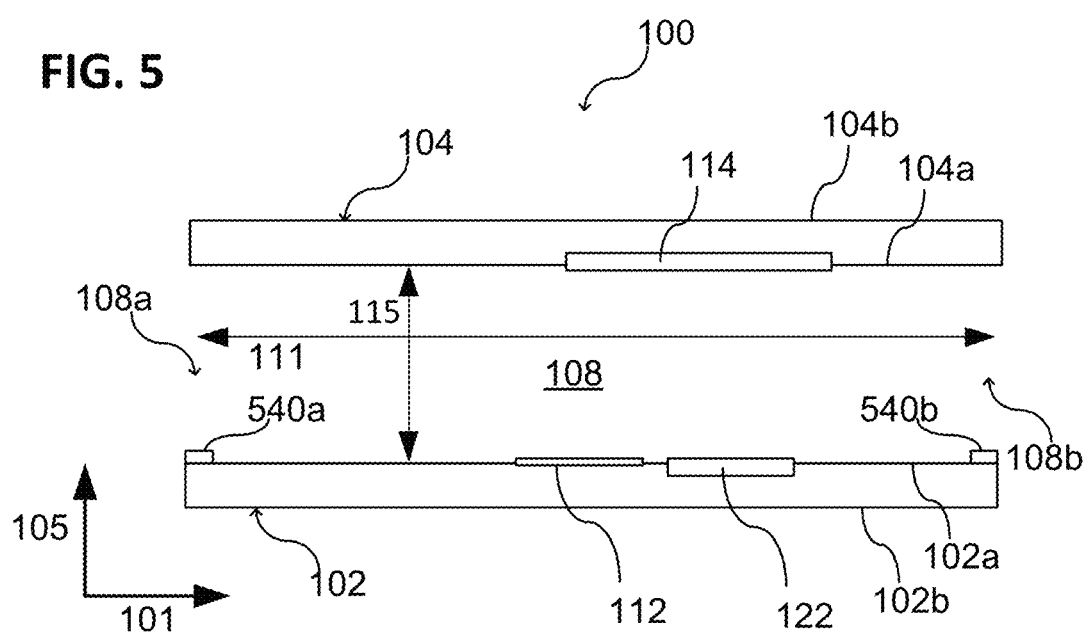
FIG. 5 shows a particle sensor in a schematic cross sectional view, according to various embodiments.

According to various embodiments, the particle sensor 100 may further include at least one temperature sensor configured to measure a temperature of a fluid that flows in the micro-channel 108. As illustrated in FIG. 5, the particle sensor 100 as described before, e.g. with reference to FIG. 2A, may further include at least two temperature sensors 540a, 540b, wherein a first temperature sensor 540a of the at least two temperature sensors 540a, 540b is configured to measure a temperature of the fluid at the first opening 108a of the at least two openings 108a, 108b and wherein a second temperature sensor 540b of the at least two temperature sensors 540a, 540b is configured to measure a temperature of the fluid at the second opening 108b of the at least two openings 108a, 108b.

According to various embodiments, at least one temperature sensor may be integrated into the first carrier 102. Alternatively, the at least one temperature sensor may be integrated into the second carrier 104. Alternatively, a plurality of temperature sensors may be integrated into the first carrier 102 and/or into the second carrier 104. Further, more than two temperature sensors 540a, 540b may be used for measuring a temperature distribution of the fluid in the channel 108, e.g. two disposed over and/or in the first carrier 102 and another two disposed over and/or in the second carrier 104 near the openings 108a, 108b respectively. Other implementations may be provided to monitor the air flow by temperature sensors. The temperature sensors may be positioned at the entrance 108a and at the outlet 108b of the channel region 108 and, e.g. optionally, in between.

According to various embodiments, the one or more heating structures 112 may be fabricated using a silicon-on-nothing technique (e.g. a so-called venezia process or an empty space in silicon process). Alternatively, the one or more heating structures 112 may include a poly silicon plate respectively separated from the underlying carrier or layer by at least one cavity.

According to various embodiments, a silicon-on-insulator wafer may be used to form the one or more heating structures 112. The silicon-on-insulator wafer may have a silicon region and a silicon top layer, wherein an insulator layer is disposed between the silicon region and the silicon top layer. The silicon top layer of the silicon-on-insulator wafer can be used as a functional layer for the one or more heating structures 112 and for the one or more light detecting structures 122. An etching process from the backside of the silicon-on-insulator wafer (i.e. through the silicon region) may be used to remove portions of the silicon-on-insulator wafer. The etching process may stop at the insulator layer (e.g. at a buried oxide layer) as it can be selective only to silicon. Portions of the oxide that are not removed are used as the spacer structure 106 described herein. The illuminating unit 304 may be mounted to the backside of the silicon-on-insulator wafer.

FIG. 6A illustrates a heating structure 112 in a schematic cross sectional view, according to various embodiments. The heating structure 112 may include a first layer 602, a second layer 604, and at least one cavity 603 (i.e. a cavity structure including at least one cavity 603) disposed between the first layer 602 and the second layer 604. The at least one cavity 603 may be free of any solid material. The at least one cavity 603 may be free of any liquid material. Therefore, the at least one cavity 603 may be configured as a thermally insulating structure.

The heating structure 112 may further include an isolation structure 606 disposed over, e.g. directly on, the first layer 602. The isolation structure 606 may connect the second layer 604 to the first layer 602. The isolation structure 606 may be configured to fix the first layer 602 to the second layer 604 or, in other words, to carry the second layer 604 spaced apart from the first layer 604. According to various embodiments, the isolation structure 606 may physically connect the second layer 604 to the first layer 602, wherein the second layer 604 may not have a direct physical contact to the first layer 602. The isolation structure 606 may also define a distance between the first layer and the second layer or in other words a height 603h of the at least one cavity 603. The height 603h of the at least one cavity 603 or cavity structure 603 may be in the range from about 100 nm to about 15 µm, e.g. in the range from about 0.5 µm to about 15 µm, e.g. in the range from about 0.5 µm to about 2 µm.

As illustrated in FIG. 6A, the cavity structure 603 and the isolation structure 606 may thermally isolate the second layer 604 from the first layer 602. Therefore, the second layer 604 may be used as a heating layer (also referred to as heating element or heater), as described herein. According to various embodiments, the heating structure 112 may further include an electrode structure 608. The electrode structure 608 may electrically contact the second layer 604 to provide an electrical current through the second layer 604. The electrode structure 608 may include at least two electrical contacts spaced apart from each other (e.g. more than 50 µm) so that an electrical current may substantially flows through the second layer 604.

According to various embodiments, the at least one cavity 603 may be air-tightly sealed by the arrangement of the first layer 602, the second layer 604, and the isolation structure 606. In other words, the isolation structure 606 may completely surround the at least one cavity 603 and may be in physical contact with both the first layer 602 and the second layer 604. Further, a vacuum (i.e. sub-atmospheric pressure, e.g. a pressure less than about 100 mbar) may be provided within the air-tightly sealed at least one cavity 603. This may be achieved by sealing the at least one cavity 603 during semiconductor manufacturing in a vacuum processing chamber of a semiconductor processing tool, for example by using a vacuum coating tool, e.g. a tool for chemical vapor deposition or physical vapor deposition.

According to various embodiments, the first layer 602 may be the first carrier 102, part of the first carrier 102, or disposed over the first carrier 102, as described with reference to FIG. 2A. A first surface 604a of the second layer 604 may be exposed to the channel 108, as described herein. A second surface 604b of the second layer 604 may be exposed to the at least one cavity 603. The second layer 604 may be also configured as a multilayer stack including at least one heating layer. The heating layer may include polycrystalline silicon. The isolation structure 606 may electrically isolate the second layer 604 from the first layer 602.

Further, as illustrated in FIG. 6D, the electrode structure 608 may be arranged or configured to laterally contact the second layer 604.

The at least one cavity of the particle sensor 100 as illustrated in FIGS. 6A and 6D may be formed base on a sacrificial layer process, as described exemplarily with reference to FIG. 6B and FIG. 6C. First the isolation structure 606 and a sacrificial layer may be formed over a surface 602a of the first layer 602. The isolation structure 606 may laterally surround the sacrificial layer 613. The sacrificial layer 613 may include any suitable material that can be easily and selectively etched with respect to the isolation structure 606, and the first and second layer 602, 604. The isolation structure 606 may include a thermally insulating material, e.g. an oxide, e.g. silicon oxide. The second layer 604 may be formed, e.g. deposited, over the isolation structure 606 and the sacrificial layer 613. The second layer 604 may include for example polysilicon or any other material suitable to be heated via an electrical current. Subsequently, the sacrificial layer 613 may be selectively removed, e.g. via wet etching or plasma etching. Therefore, an access (e.g. an opening) may be formed through the first layer 602, the second layer 604 or the isolation structure 606. After the sacrificial layer 613 has been partially or completely removed, the access may be closed (e.g. via depositing material of the access) to seal the cavity 603 if desired.

FIG. 7A illustrates a heating structure 112 in a schematic cross sectional view, according to various embodiments. The heating structure 112 may include a first layer 602, a second layer 604, and at least one cavity 603 disposed between the first layer 602 and the second layer 604, in analogy to the embodiments described before.

The heating structure 112 may further include an isolation structure 606 disposed between the first layer 602 and the second layer 604. The isolation structure 606 may (e.g. laterally) connect the second layer 604 to the first layer 602. The isolation structure 606 may be configured to fix the second layer 602 to the first layer 604 or, in other words, to carry the second layer 604 spaced apart from the first layer 604. According to various embodiments, the isolation structure 606 may physically connect the second layer 604 to the first layer 602, wherein the second layer 604 may not have a direct physical contact to the first layer 602. The height 603h of the at least one cavity 603 or cavity structure 603 may be in the range from about 100 nm to about 15 μm, e.g. in the range from about 0.5 μm to about 15 μm, e.g. in the range from about 0.5 μm to about 2 μm.

As illustrated in FIG. 7A, the cavity structure 603 and the isolation structure 606 may thermally isolate the second layer 604 from the first layer 602. Therefore, the second layer 604 may be used as a heating layer (also referred to as heating element or heater), as described herein. According to various embodiments, the heating structure 112 may further include an electrode structure 608 that electrically contacts the second layer 604. Therefore, an electrical current may be conducted through the second layer 604 via the electrode structure 608. The electrode structure 608 may include at least two electrical contacts spaced apart from each other (e.g. more than 50 μm) so that an electrical current substantially flows through the second layer 604.

According to various embodiments, the at least one cavity 603 may be air-tightly sealed by the arrangement of the first layer 602, the second layer 604 and the isolation structure 606. Therefore, the isolation structure 606 may completely laterally surround the second layer 604 and may be in physical contact with both the first layer 602 and the second layer 604. Further, a vacuum (i.e. sub-atmospheric pressure, e.g. a pressure less than about 100 mbar) may be provided within the air-tightly sealed at least one cavity 603. This may be achieved by sealing the at least one cavity 603 during semiconductor manufacturing in a vacuum processing chamber of a semiconductor processing tool, for example by using a vacuum coating tool, e.g. a tool for chemical vapor deposition or physical vapor deposition.

According to various embodiments, the first layer 602 may be the first carrier 102, a part of the first carrier 102, or disposed over the first carrier 102, as described with reference to FIG. 2A. A first surface 604a of the second layer 604 may be exposed to the channel 108, as described herein. A second surface 604b of the second layer 604 may be exposed to the at least one cavity 603. The isolation structure 606 may also electrically isolate the second layer 604 from the first layer 602.

The at least one cavity 603 of the particle sensor 100 illustrated in FIG. 7A may be formed as described with reference to FIG. 7B and FIG. 7C.

At least one cavity 603 may be provided in the first layer 602. The first layer 602 may include silicon. The at least one cavity 603 may be formed by a silicon-on-nothing process, e.g. by forming a trench structure in the carrier and by annealing the trench structure so that at least one cavity is formed during the annealing by migration and/or diffusion of the silicon. However, there may be other techniques suitable for forming one or more cavities 603 in the first layer 602. According to various embodiments, the at least one cavity 603 may be completely surrounded by material of the first carrier 602, therefore, the at least one cavity 603 may be referred to as a buried cavity.

Subsequently, the isolation structure 606 may be formed in the first layer 602. Therefore, a trench structure may be formed that extends from a surface 602a of the first layer 602 into the first layer 602. The trench structure may laterally surround the second layer 604. Illustratively, the trench structure may laterally surround a first region 604 of the first layer 602. The trench structure may extend at least to the at least one cavity 603. The trench structure may be completely filled or at least partially filled with a thermally insulating material, e.g. with an oxide, e.g. silicon oxide, to provide the isolation structure 606.

Figure 7D:
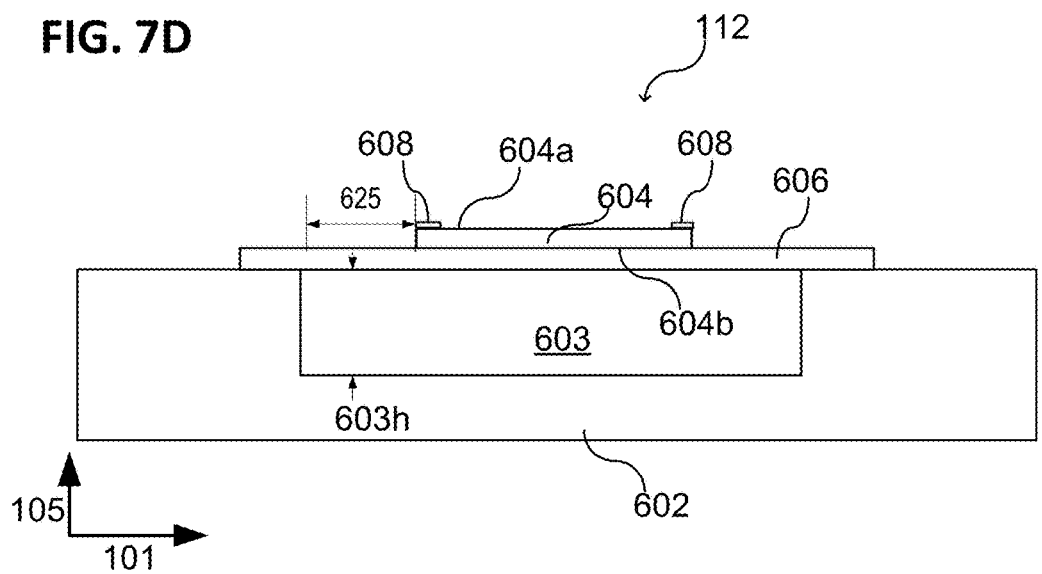
FIGS. 7D to 7F respectively show a heater structure of a particle sensor in a schematic cross sectional view, according to various embodiments.

FIG. 7D illustrates a heating structure 112 in a schematic cross sectional view, according to various embodiments. The heating structure 112 may include a first layer 602, a second layer 604, and at least one cavity 603 disposed between the first layer 602 and the second layer 604, in analogy to the embodiments described before.

The heating structure 112 may further include an isolation structure 606 disposed between the first layer 602 and the second layer 604. The isolation structure 606 may connect the second layer 604 to the first layer 602. The isolation structure 606 may be configured to fix the second layer 602 to the first layer 604 or, in other words, to carry the second layer 604 spaced apart from the first layer 604. According to various embodiments, the isolation structure 606 may physically connect the second layer 604 to the first layer 602, wherein the second layer 604 may not have a direct physical contact to the first layer 602. The at least one cavity 603 may be disposed between the isolation structure 606 and the first layer 602. In other words, the isolation structure 606 and the first layer 602 may surround (e.g. completely) the at least one cavity 603.

Further, a vacuum (i.e. sub-atmospheric pressure, e.g. a pressure less than about 100 mbar) may be provided within the at least one cavity 603. This may be achieved by air-tightly sealing the at least one cavity 603 during semiconductor manufacturing in a vacuum processing chamber of a semiconductor processing tool, for example by using a vacuum coating tool, e.g. a tool for chemical vapor deposition or physical vapor deposition.

The height 603h of the at least one cavity 603 or cavity structure 603 may be in the range from about 100 nm to about 15 µm, e.g. in the range from about 0.5 µm to about 15 µm, e.g. in the range from about 0.5 µm to about 2 µm.

As illustrated in FIG. 7D, the cavity structure 603 and the isolation structure 606 may thermally isolate the second layer 604 from the first layer 602. Therefore, the second layer 604 may be used as a heating layer (also referred to as heating element or heater), as described herein. According to various embodiments, the heating structure 112 may further include an electrode structure 608 that electrically contacts the second layer 604. Therefore, an electrical current may be conducted through the second layer 604 via the electrode structure 608. The electrode structure 608 may include at least two electrical contacts spaced apart from each other (e.g. more than 50 nm) so that an electrical current substantially flows through the second layer 604.

According to various embodiments, the at least one cavity 603 may be air-tightly sealed by the arrangement of the first layer 602 and the isolation structure 606. In this case, the first layer 602 may completely laterally surround the at least one cavity 603; and, further, the isolation structure 606 may completely cover the at least one cavity 603 disposed within the first layer 602. The isolation structure 606 may be in physical contact with both the first layer 602 and the second layer 604. Further, a vacuum (i.e. sub-atmospheric pressure, e.g. a pressure less than about 100 mbar) may be provided within the air-tightly sealed at least one cavity 603. This may be achieved by sealing the at least one cavity 603 during semiconductor manufacturing in a vacuum processing chamber of a semiconductor processing tool, for example by using a vacuum coating tool, e.g. a tool for chemical vapor deposition or physical vapor deposition.

According to various embodiments, the first layer 602 may be the first carrier 102, a part of the first carrier 102, or disposed over the first carrier 102, as described with reference to FIG. 2A. A first surface 604a of the second layer 604 may be exposed to the channel 108, as described herein. A second surface 604b of the second layer 604 may be in contact with the isolation structure 606. The isolation structure 606 may also electrically isolate the second layer 604 from the first layer 602.

The second layer 604 may be a plate structure used as a heating layer or heater plate. The plate structure 604 may be thermally isolated from the first layer 602 via the at least one cavity 603 and the isolation structure 606. The isolation structure 606 may be an oxide frame or an oxide layer. The plate structure 604 may include polysilicon. The plate structure 604 may have a length (e.g. along direction 101) and a width (e.g. perpendicular to directions 101, 105) respectively in the range from about 250 µm to about 750 µm, e.g. of about 500 µm. The oxide frame 606 may have a thickness in the range from about 0.25 µm to about 2 µm, e.g. of about 1 µm. The oxide frame 606 may have a length (e.g. along direction 101) and a width (e.g. perpendicular to directions 101, 105) respectively in the range from about 500 µm to about 1000 µm. According to various embodiments, the plate structure 604 (i.e. the second layer) may be laterally spaced apart from the first layer 602. A lateral distance 625 from a side of the cavity 603 to a respective side of the plate structure 604 may be in the range from about 1 µm to about 50 µm, e.g. in the range from about 5 µm to about 20 µm. The lateral distance may reduce a heat transfer from the plate structure 604 to the first layer 602 via the isolation structure 606.

According to various embodiments, the second layer 604 may be heated up to about 100 K above the environment temperature, e.g. 100 K above the temperature of the first layer 602. The environment temperature may be for example about 300 K and the second layer 604 may be heated up to about 400 K via an electrical current provided through the second layer 604.

Figure 7E:
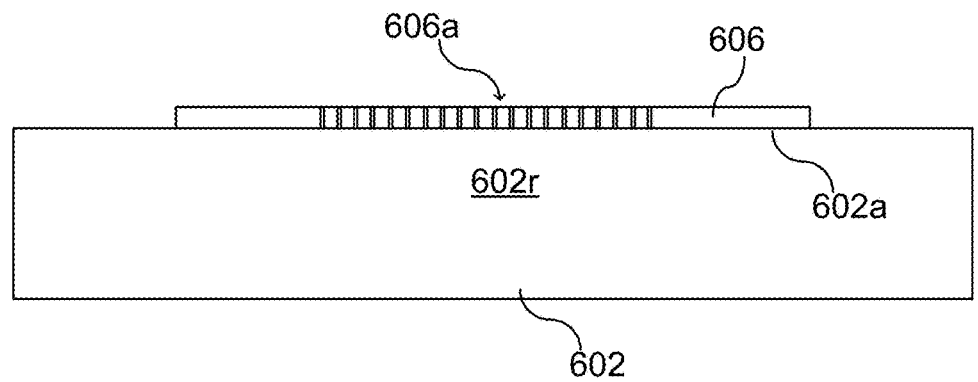
Figure 7F:
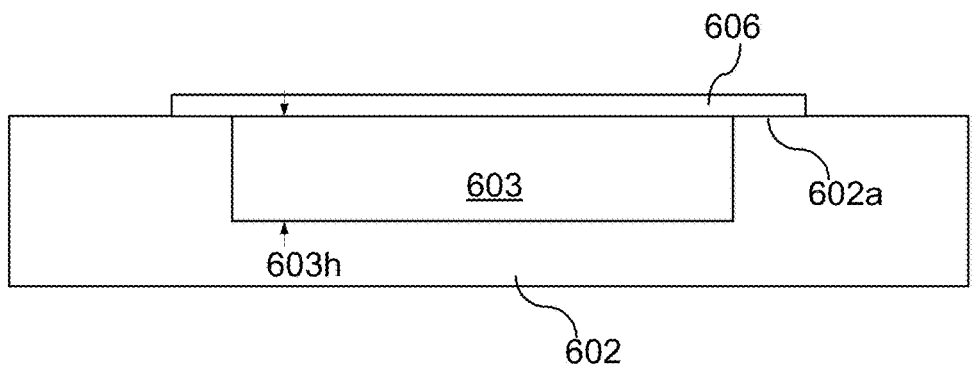

The at least one cavity 603 of the particle sensor 100 illustrated in FIG. 7D may be formed as described with reference to FIG. 7E and FIG. 7F.

First, the isolation structure 606 may be formed over a surface 602a the first layer 602. The isolation structure 606 may be patterned in a region 606a to partially expose the surface 602a of the first layer below the isolation structure 606. The patterned region may include a plurality of through holes providing an access for an etchant to partially remove the first layer in a region 602r below region 606a of the isolation structure 606.

Subsequently, the first layer 602 may be partially removed, e.g. via a selective wet etch process or via a selective dry etch process, to provide the at least one cavity 603 in the first layer 602. Optionally, the plurality of through holes in the isolation structure 606 may be filled (e.g. completely), thereby providing a dense (i.e. air-impermeable, hermetic, or air-tight) isolation structure 606 covering the cavity 603. The respective through holes in the isolation structure 606 may be filled with a thermally isolating material or any other suitable material, e.g. with an oxide or a nitride, e.g. with the same material as used for forming the isolation structure 606, e.g. with silicon oxide or silicon nitride. However, the materials forming the isolation structure 606 may be selected to thermally isolate the second layer 604 from the first layer 602.

Subsequently, the second layer 604 may be formed over the isolation structure 606, e.g. via deposition and patterning a polycrystalline silicon layer. According to various embodiments, the second layer 604 may be at least partially embedded into the isolation structure 606 or may be disposed on the isolation structure 606.

According to various embodiments, a pressure of less than about 1 mbar may be provided in the cavity 603 before the cavity is sealed by filling the respective through holes in the isolation structure 606. According to various embodiments, a vacuum may be provided in the respective cavity 603 in such a way that the mean free path of the remaining gas molecules in the cavity 603 may be greater than the height 603h of the cavity 603. At a pressure of pressure of less than about 1 mbar, the mean free path of the remaining gas molecules in the cavity 603 may be greater than about 60 µm.

Figure 8A:
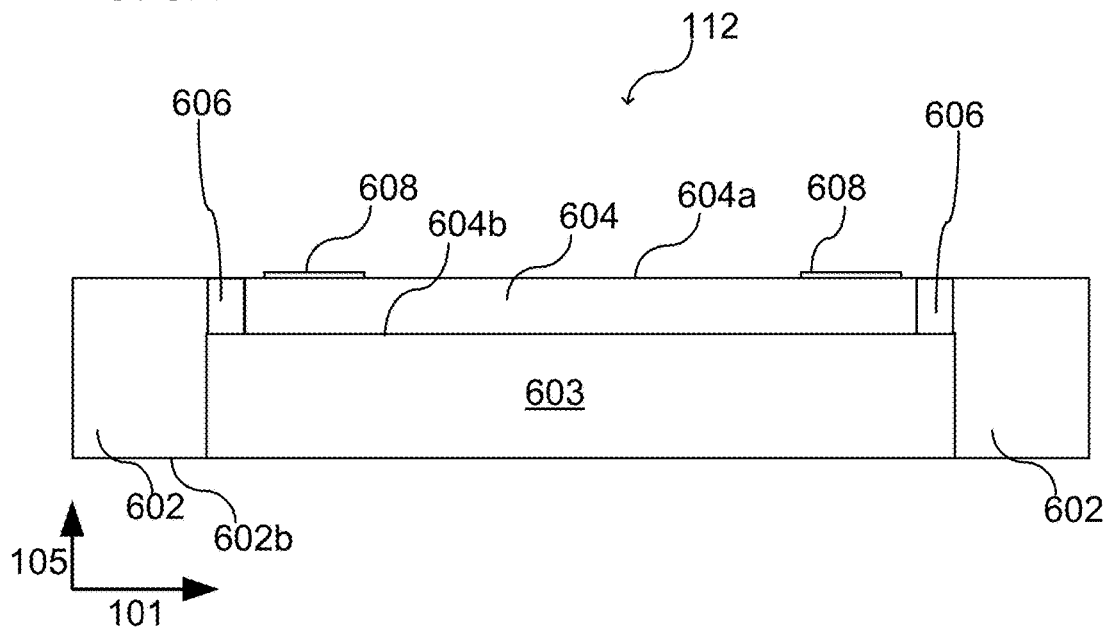
FIGS. 8A to 8C respectively show a heater structure of a particle sensor in a schematic cross sectional view, according to various embodiments.

FIG. 8A illustrates a heating structure 112 in a schematic cross sectional view, according to various embodiments. The heating structure 112 may include a first layer 602 and a second layer 604, as describe before.

The heating structure 112 may further include an isolation structure 606 disposed between the first layer 602 and the second layer 604. The isolation structure 606 may (e.g. laterally) connect the second layer 604 to the first layer 602. The isolation structure 606 may be configured to fix the second layer 602 to the first layer 604 or, in other words, to carry the second layer 604 spaced apart from the first layer 604. According to various embodiments, the isolation structure 606 may physically connect the second layer 604 to the first layer 602, wherein the second layer 604 may not have a direct physical contact to the first layer 602.

As illustrated in FIG. 8A, the isolation structure 606 may thermally isolate the second layer 604 from the first layer 602. Therefore, the second layer 604 may be used as a heating layer, as described herein. According to various embodiments, an electrode structure 608 may be provided that electrically contacts the second layer 604 to provide an electrical current through the second layer 604. The electrode structure 608 may include at least two electrical contacts spaced apart from each other (e.g. more than 50 μm) so that an electrical current substantially flows through the second layer 604.

At least one cavity 603 may be provided below the second layer 604. The at least one cavity 603 may be formed in the first layer 602. The at least one cavity 603 may extent from a second surface 602b of the first layer 602 into the first layer 602. The at least one cavity 603 may thermally isolate the second layer 604, e.g. by preventing or reducing heat conduction. According to various embodiments, the isolation structure 606 may completely laterally surround the second layer 604 and may be in physical contact to both the first layer 602 and the second layer 604.

According to various embodiments, the first layer 602 may be the first carrier 102 part of the first carrier 102, as described before. A first surface 604a of the second layer 604 may be exposed to the channel 108, as described herein. A second surface 604b of the second layer 604 may be exposed to the at least one cavity 603. The isolation structure 606 may electrically isolate the second layer 604 from the first layer 602.

Figure 8B:
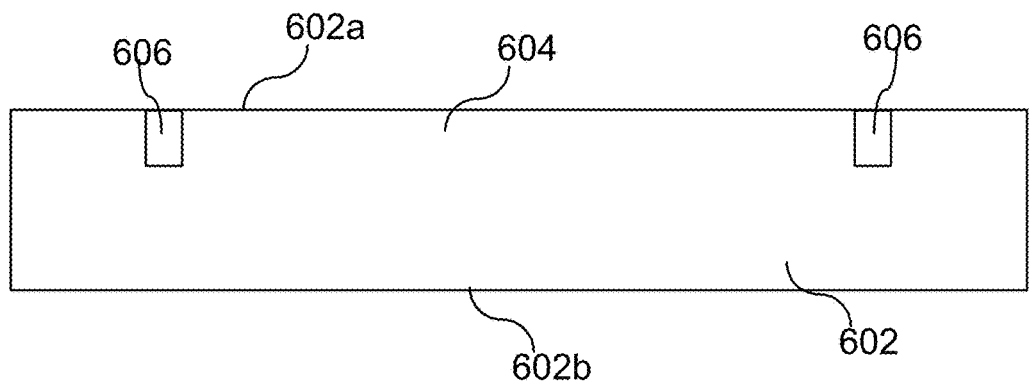
Figure 8C:
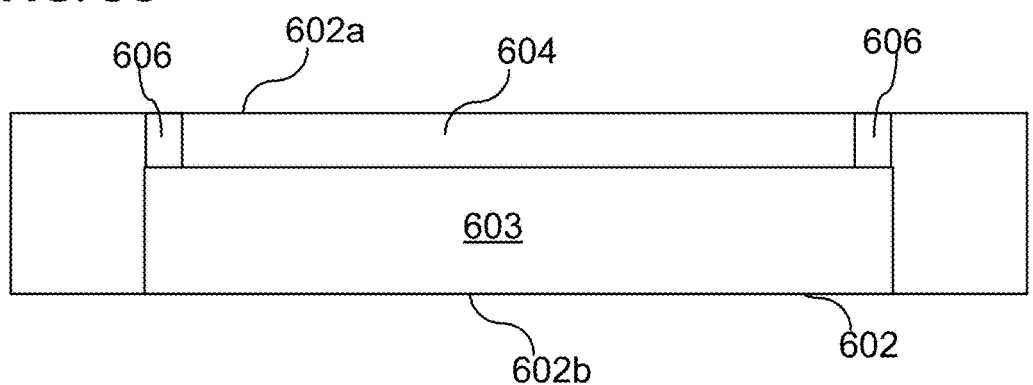

The at least one cavity 603 of the particle sensor 100 as illustrated in FIG. 8A may be formed as described with reference to FIG. 8B and FIG. 8C.

The isolation structure 606 may be formed in the first layer 602. Therefore, a trench structure may be formed that extends from a first surface 602a of the first layer 602 into the first layer 602. Illustratively, the trench structure may laterally surround a region 604 of the first layer 602. The trench structure may be completely filled or at least partially filled with a thermally insulating material, e.g. an oxide, e.g. silicon oxide, to provide the isolation structure 606.

The at least one cavity 603 may be formed from a second surface 602b of the first layer 602 into the first layer 602, e.g. via reactive ion etching. The first layer 602 may have a thickness that may require the use of a so called Bosch-Process or deep reactive ion etching to form a sufficiently deep cavity 603 into the first layer 602. According to various embodiments, an etch stop layer may be used in the first layer 602 to limit the etching of the at least one cavity 603.

FIG. 9A illustrates the particle sensor 100 in a schematic cross sectional view, according to various embodiments, wherein the particle sensor 100 is configured in a similar way as described with reference to FIG. 2A or FIG. 5. According to various embodiments, the at least one heating structure 112 and the at least one light detecting structure 122 may be embedded into a planar encapsulation layer 902 to prevent or reduce distortions of the fluid flow in the micro-channel 108. The planar encapsulation layer 902 may include a transparent oxide, e.g. silicon oxide. Further, according to various embodiments, the light detecting structure 114 may be embedded into a further planar encapsulation layer 904 to prevent or reduce distortions of the fluid flow in the micro-channel 108. The further planar encapsulation layer 904 may include a transparent oxide, e.g. silicon oxide.

FIG. 9B illustrates the particle sensor 100 in a schematic cross sectional view, according to various embodiments, wherein the particle sensor 100 is configured in a similar way as described with reference to FIG. 2A or FIG. 5. According to various embodiments, a light blocking layer 934 may be provided in the first carrier 102, e.g. below the at least one light detecting structure 122. The light blocking layer 934 may reduce or prevent light introduction through the first carrier 102 into the light detecting structure 122. Therefore, the light detecting structure 122 may be operated with high accuracy.

According to various embodiments, the at least one heating structure 112 may be configured to dissipate as less heat as possible into the first carrier 102. This may be achieved for example by using the heating structures 112 or similar heating structures as described herein with reference for example to FIGS. 6A to 8C. The heating structures 112 may have a heating layer 604 (or generally a heating element) that is thermally isolated from the first carrier 102. This arrangement may enhance the sensitivity of the light detecting structure 122, since heat transfer from the heating structures 112 to the light detecting structures may be reduced. Heat that would be transferred into the light detecting structures could reduce for example the resolution of light detecting structures, e.g. including an optical sensor, such as a photo diode, due to an increased thermal noise.

FIG. 9C illustrates the particle sensor 100 in a schematic cross sectional view, according to various embodiments, wherein the particle sensor 100 is configured in a similar way as described with reference to FIG. 2A. According to various embodiments, the one or more heating structures 112 and the one or more light detecting structure 122 may be integrated side by side into the same carrier 102, e.g. into a wafer, e.g. into a silicon wafer. According to various embodiments, a heat sink structure 944 may be provided at the second surface 102b of the first carrier 102 to enhance heat dissipation from the first carrier 102 during operation. This may allow for example a high resolution of an optical sensor, such as a photo diode, due to a decreased thermal noise.

FIG. 9D illustrates the particle sensor 100 in a schematic cross sectional view, according to various embodiments, wherein the particle sensor 100 is configured in a similar way as described with reference to FIG. 2A and FIG. 3. According to various embodiments, at least a first light detecting structure 122a may be used to directly measure a shading 924d caused by particles 308p moving through the channel 108.

The first light detecting structure 122a may include at least one photo diode 922, or any other suitable light detecting element, and, optionally, an aperture 926 to reduce the maximal incident angle for light detection. Correspondingly, the light emitting structure 114 may be arranged at the opposite side of the channel 108 in such a way that light 924 is emitted substantially into the direction of the first light detecting structure 122a. The light emitting structure 114 may include at least one light emitting diode 914, or any other suitable light emitting element, and, optionally, an aperture 916 to reduce the maximal emission angle of the at least one light emitting diode 914. This arrangement of the first light detecting structure 122a relative to the light emitting structure 114 may allow to count particles passing through the channel 108, e.g. by analyzing the first light intensity measured by the first light detecting structure 122a.

Further, e.g. simultaneously, a second light detecting structure 122b may be used to measure stray light 924s reflected by the particles 308p. The second light detecting structure 122b may include at least one photo diode 922, or any other suitable light detecting element.

Further, according to various embodiments, micro-optical elements like lenses, apertures, mirrors, and the like may be used to support the dual-detecting configuration of the particle sensor 100 so that stray light 324s may be detected substantially (e.g. only) by the second light detecting structure 122*b* and that direct light 324*d*, and therefore the shading caused by the particles 308*p*, may be detected substantially (e.g. only) by the first light detecting structure 122*a*. This may allow counting light-colored particles 308*p* by detecting stray light 324*s* and dark-colored particles 308*p* by detecting the shadowing of the direct light 324*d*.

The particle sensor 100 and the integrated heating structures 122 described herein may support an integration of particle sensors with minimum foot print for next generation products and devices. A combination of, for example, heaters and photo diodes on a silicon carrier 102 (e.g. on a die, on a chip, or on any other silicon workpiece) may be used together with a light emitting diode that is mounted on a structured spacer 106 face to face to the silicon carrier 102. The enclosed channel 108 may be used as a monitored volume having free convective air flow.

According to various embodiments, a poly silicon sheet 604 disposed above a cavity may be used as heating element or heating layer. In a similar way, an array of poly silicon sheets may be disposed above extended cavities.

Figure 10A:
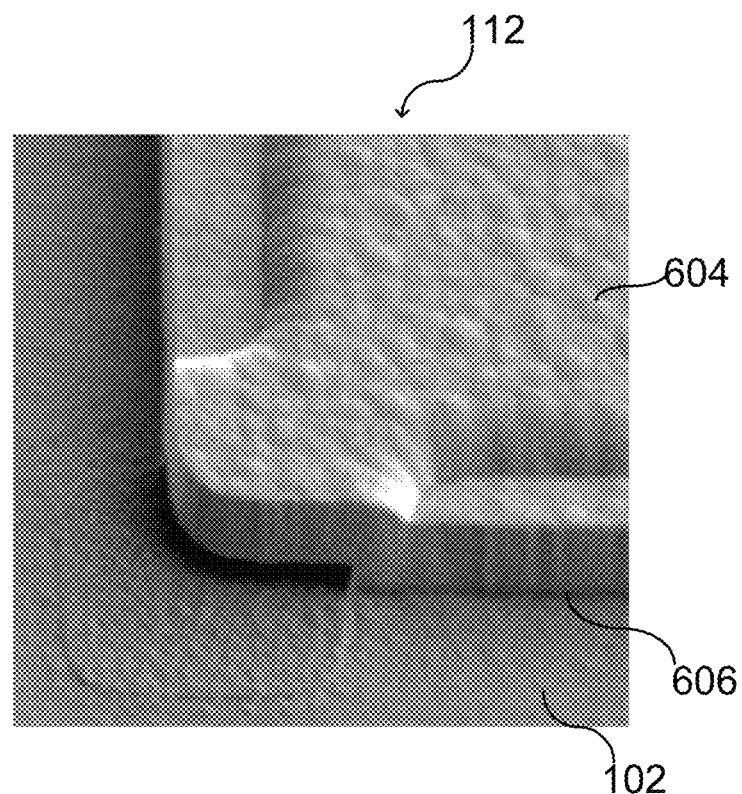
FIGS. 10A and 10B respectively show an electron microscopy image of a particle sensor and a heater structure, according to various embodiments.
Figure 10B:
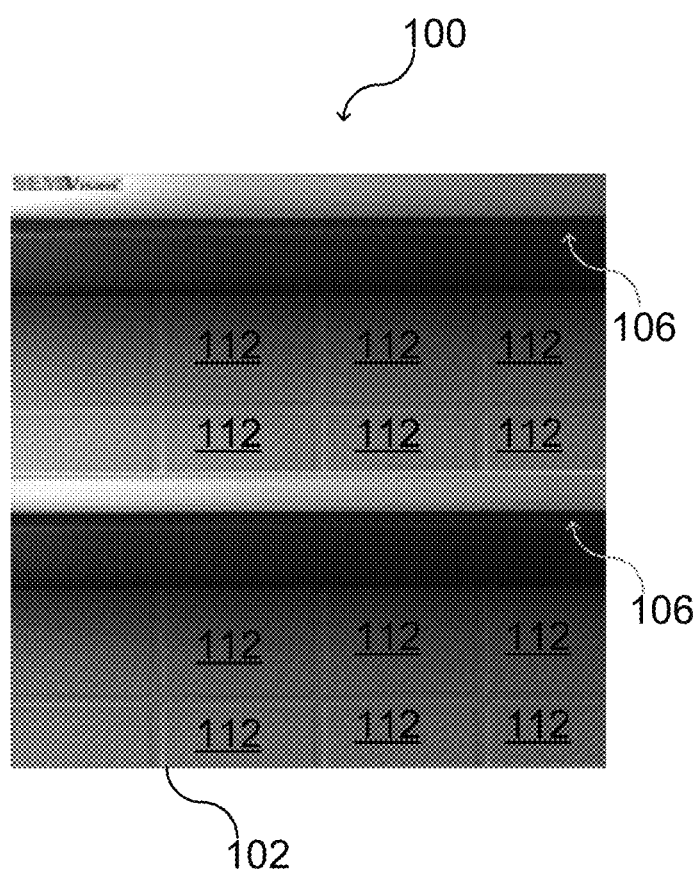

FIG. 10A and FIG. 10B respectively show scanning electron microscope images of exemplary heater 112 and particle sensor 100 constructions. As illustrated in FIG. 10A, a heater plate 604 (e.g. made of poly silicon) may be disposed on a substrate 102 (e.g. on a silicon substrate), wherein a thermal isolation structure 606 (e.g. based on a thermally insulating oxide) may be disposed between the heater plate 604 and the substrate 102. At the corner of the heater plate 604 there is the release opening (also referred to as access) for removal of a used sacrificial layer during processing. As illustrated in FIG. 10B, an array of heater structures 112 may be formed over and/or in the first carrier 102. A spacer material 106 is disposed on top of the carrier. The light detecting structures 122 may be formed between and/or below the heater structures 112.

FIG. 11 illustrates a schematic flow diagram of a method 1100 for sensing a particle concentration or a number of particles in a fluid. The method may be carried out based on the particle sensor 100 as described herein, e.g. with reference to FIG. 9D. The method may include: in 1110, heating at least one heating structure 112 of a particle sensor 100 to provide a free convection flow of the fluid in a channel 108 of the particle sensor 100, wherein the fluid includes particles 308*p*; in 1120, emitting light into the channel 108 of the particle sensor 100 by a light emitting structure 114 of the particle sensor 100; in 1130, detecting a first light intensity of the light emitted by the light emitting structure 114 by a first light detecting structure 122*a* of the particle sensor 100, wherein the first light detecting structure 122*a* is arranged to receive light directly from the light emitting structure 114; and, in 1140, detecting a second light intensity of the light emitted by the light emitting structure 114 by a second light detecting structure 122*b* of the particle sensor 100, wherein the second light detecting structure 122*b* is arranged to receive substantially light from the light emitting structure 114 that is scattered on particles 308*p* in the channel 108.

FIG. 12 illustrates a schematic flow diagram of a method 1200 for sensing a particle concentration or a number of particles in a fluid. The method may be carried out based on a plurality of particle sensors 100, as described herein. According to various embodiments, at least two or more than two particle sensors 100 may be provided on a carrier in a similar configuration as described herein exemplarily for one particle sensor 100 with one channel 108. The at least two particle sensors 100 may be substantially equal to one another but may be operated under different conditions, e.g. at different temperatures. Therefore, the at least two particle sensors 100 may be used to detect particles with different diameters, as described for example with reference to FIG. 4, to control different flow velocities for the free convection of the fluid to be analyzed. The method may include: in 1210, heating a first heating structure of a first particle sensor to a first temperature thereby providing a first free convection flow of the fluid in a first channel of the first particle sensor; in 1220, emitting light into the first channel of the first particle sensor by a first light emitting structure of the first particle sensor; in 1230, detecting a first light intensity of the light emitted by the first light emitting structure by a first light detecting structure of the first particle sensor; in 1240, heating a second heating structure of a second particle sensor to a second temperature thereby providing a second free convection flow of the fluid in a second channel of the second particle sensor; in 1250, emitting light into the second channel of the second particle sensor by a second light emitting structure of the second particle sensor; and, in 1260, detecting a second light intensity of the light emitted by the second light emitting structure by a second light detecting structure of the second particle sensor, wherein the first temperature is less than the second temperature.

FIG. 13 illustrates a schematic flow diagram of a method 1300 for sensing a particle concentration or a number of particles in a fluid. The method may be carried out based on a plurality of particle sensors 100 as described herein. According to various embodiments, at least two or more than two particle sensors 100 may be provided on a carrier in a similar configuration as described herein exemplarily for one particle sensor 100 with one channel 108. The at least two particle sensors 100 may be operated under substantially equal conditions, e.g. at the same temperatures, but may be provided with different geometries (i.e. dimensions) of the channel. Therefore, the at least two particle sensors 100 may be used to detect particles with different diameters, as described for example with reference to FIG. 4, to generate different flow velocities for the free convection of the fluid to be analyzed. The method may include: in 1310, heating a first heating structure of a first particle sensor thereby providing a first free convection flow of the fluid in a first channel of the first particle sensor; in 1320, emitting light into the first channel of the first particle sensor by a first light emitting structure of the first particle sensor; in 1330, detecting a first light intensity of the light emitted by the first light emitting structure by a first light detecting structure of the first particle sensor; in 1340, heating a second heating structure of a second particle sensor thereby providing a second free convection flow of the fluid in a second channel of the second particle sensor; in 1350, emitting light into the second channel of the second particle sensor by a second light emitting structure of the second particle sensor; and, in 1360, detecting a second light intensity of the light emitted by the second light emitting structure by a second light detecting structure of the second particle sensor, wherein the first channel has a greater dimension than the second channel.

According to various embodiments, methods 1200 and 1300 may further include determining a number of the particles or a concentration of the particles based on the detected first light intensity and second light intensity.

Example 1 is an integrated heating structure. The integrated heating structure may include a first layer; a second layer; a cavity structure disposed between the first layer and the second layer, wherein the cavity structure includes at least one cavity that is free of solid material; an isolation structure laterally surrounding the second layer, wherein the isolation structure physically connects the second layer to the first layer, wherein the cavity structure and the isolation structure thermally isolates the second layer from the first layer; and an electrode structure electrically contacting the second layer to provide an electrical current through the second layer. The at least one cavity may be air-tightly sealed by the arrangement of the first layer, the second layer and the isolation structure. Further, a vacuum (i.e. sub-atmospheric pressure, e.g. a pressure less than about 100 mbar) may be provided within the air-tightly sealed at least one cavity.

Alternatively, the integrated heating structure may include a first layer; a second layer spaced apart from the first layer; at least one cavity disposed between the first layer and the second layer, wherein the at least one cavity is free of solid material; a fixation structure physically connecting the second layer to the first layer, wherein the fixation structure is configured to thermally isolate the second layer from the first layer; and an electrode structure electrically contacting the second layer to provide an electrical current through the second layer. The at least one cavity may be air-tightly sealed by the arrangement of the first layer, the second layer and the fixation structure. Further, a vacuum (i.e. sub-atmospheric pressure, e.g. a pressure less than about 100 mbar) may be provided within the air-tightly sealed at least one cavity.

Alternatively, the integrated heating structure may include a carrier; an isolation structure disposed in the carrier, the isolation structure laterally surrounding a region of the carrier and separating the region of the carrier from the rest of the carrier; wherein the carrier includes at least one cavity disposed below the region of the carrier; wherein the at least one cavity is free of solid material; and an electrode structure electrically contacting the region of the carrier to provide an electrical current through the region. In this case, the isolation structure laterally surrounding a first region of the carrier and separating the first region of the carrier from a second region of the carrier. The second region may at least laterally surround the first region. The second region may be optionally disposed below the first region. The isolation structure may extend from a first surface of the carrier into the carrier. The at least one cavity may extend from a second surface of the carrier into the carrier, wherein the second surface is opposite the first surface.

Alternatively, the integrated heating structure may include a carrier; a cavity structure disposed in the carrier, the cavity structure including at least one cavity that is free of solid material; a trench structure extending from a surface of the carrier into the carrier at least to the cavity structure, the trench structure laterally surrounding a region of the carrier above the at least one cavity; and an electrode structure electrically contacting the region of the carrier to provide an electrical current through the region. The at least one cavity may be air-tightly sealed by the arrangement of the carrier and the trench structure. The carrier may include a first layer and a second layer disposed over the first layer. The at least one cavity may be disposed between the first layer and the second layer. Further, a vacuum (i.e. sub-atmospheric pressure, e.g. a pressure less than about 100 mbar) may be provided within the air-tightly sealed at least one cavity. The trench structure may extend from a first surface of the carrier into the carrier. The at least one cavity may extend from a second surface of the carrier into the carrier, wherein the second surface is opposite the first surface.

Alternatively, the integrated heating structure may include a carrier; an isolation structure disposed at least one of over and in the carrier; a cavity structure disposed at least one of over and in the carrier, the cavity structure including at least one cavity that is free of solid material, wherein the isolation structure adjoins the cavity structure; a heating layer disposed over the cavity structure, wherein the isolation structure thermally separates the heating layer from the carrier, and an electrode structure electrically contacting the heating layer to provide an electrical heating current through the heating layer. The heating layer may not have a direct physical contact to the carrier. As described referring to Example 1, the second layer, the (e.g. first) region of the carrier, or the heating layer may be used as a heating structure.

In Example 2, the subject matter of Example 1 can optionally include a driver circuit coupled to the electrode structure, wherein the driver circuit is configured to provide a heating current through the heating structure. The heating current may be provided in such a way, that the temperature of the heating structure is increased to a predefined temperature due to the power loss. The driver circuit may be configured to control the temperature of the heating structure. The temperature of the heating structure may be provided in the range from about 50° C. to about 300° C. to cause a free convection in the channel.

In Example 3, the subject matter of Example 1 or 2 can optionally that the driver circuit is disposed at a surface of the first layer or at a surface of the carrier. In other words, the driver circuit may be formed spaced apart from the heating structure.

In Example 4, the subject matter of any one of Examples 1 to 3 can optionally include that the isolation structure or the fixation structure includes a trench structure. The trench structure may include (e.g. may be filled with) a thermally insulating material.

In Example 5, the subject matter of any one of Examples 1 to 4 can optionally include that the isolation structure, the fixation structure, or the trench structure may completely laterally surround the heating structure. Therefore, the thermally insulating material may completely laterally surround the heating structure. Further, the heating structure may only have a direct physical contact to the isolation structure, the fixation structure, or the trench structure. In other words, the heating structure may be carried by the isolation structure, the fixation structure, or the trench structure.

In Example 6, the subject matter of any one of Examples 1 to 5 can optionally include that the isolation structure includes thermally insulating material disposed over the first layer.

In Example 7, the subject matter of Example 6 can optionally include that the thermally insulating material completely laterally surrounds the second layer and wherein the thermally insulating material physically connects the second layer to the first layer.

The thermally insulating material may include or may consist of an oxide, e.g. silicon oxide ($SiO_2$).

In Example 8, the subject matter of any one of Examples 1 to 7 can optionally include that the first layer or the carrier may include or may consist of semiconductor material, e.g. silicon.

In Example 9, the subject matter of any one of Examples 1 to 8 can optionally include that the second layer may include or may consist of semiconductor material. In other words, the heating may include or may consist of semiconductor material, e.g. silicon.

Example 10 is a particle sensor. The particle sensor may include a first carrier, the first carrier including at least one heating structure and a light detecting structure, at least one spacer structure disposed over the first carrier, a second carrier disposed over the at least one spacer structure, the second carrier including a light emitting structure, wherein the first carrier, the second carrier and the at least one spacer structure are arranged to provide a channel for a fluid flow, wherein the light emitting structure is configured to emit light into the channel, and wherein the light detecting structure is configured to detect light emitted by the light emitting structure. The light emitting structure may be integrated into the second carrier. The at least one heating structure and the light detecting structure may be (e.g. both) integrated into the first carrier. The at least one heating structure and the light detecting structure may be arranged laterally next to each other.

In Example 11, the subject matter of Example 10 can optionally include that the heating structure is configured as described in any one of Examples 1 to 9.

In Example 12, the subject matter of Example 10 or 11 can optionally include that the channel has at least two openings defining a flow direction for a fluid from one of the at least two openings to another one of the at least two openings.

In Example 13, the subject matter of Example 12 can optionally include at least two temperature sensors, wherein one of the at least two temperature sensors is configured to measure a temperature of the fluid at one of the at least two openings and wherein another one of the at least two temperature sensors is configured to measure a temperature of the fluid at another one of the at least two openings.

In Example 14, the subject matter of any one of Examples 10 to 13 can optionally include that the channel is configured to have a length in the range from about 1 mm to about 10 mm, measured for example along the flow direction.

In Example 15, the subject matter of any one of Examples 10 to 14 can optionally include that the channel is configured to have a width in the range from about 0.5 mm to about 2 mm, measured for example perpendicular to the flow direction.

In Example 16, the subject matter of any one of Examples 10 to 15 can optionally include that the channel is configured to have a height in the range from about 10 µm to about 500 µm, measured for example perpendicular to the flow direction and perpendicular to the width.

In Example 17, the subject matter of any one of Examples 10 to 16 can optionally include a driver circuit coupled to the at least one heating structure. The driver circuit may be configured to provide a heating current through the at least one heating structure.

In Example 18, the subject matter of Example 17 can optionally include that the driver circuit is configured to provide a heating current in such a way that the fluid flow in the channel has a flow velocity in the range from about 0.5 mm/s to about 5 mm/s.

In Example 19, the subject matter of any one of Examples 10 to 18 can optionally include a temperature sensor configured to measure a temperature of a fluid that flows in the channel.

In Example 20, the subject matter of any one of Examples 10 to 19 can optionally include that the at least one heating structure includes: a first layer; a second layer; a cavity structure disposed between the first layer and the second layer, wherein the cavity structure includes at least one buried cavity that is free of solid material; an isolation structure laterally surrounding the second layer, wherein the isolation structure physically connects the second layer to the first layer, wherein the cavity structure and the isolation structure separating the second layer from the first layer; and an electrode structure electrically contacting the second layer to provide an electrical current through the second layer.

In Example 21, the subject matter of Example 20 can optionally include a driver circuit coupled to the electrode structure to provide a heating current through the second layer. A driver circuit may be connected to the electrode structure and may be configured to heat the heating layer via a heating current.

In Example 22, the subject matter of Example 20 or 21 can optionally include that the driver circuit is disposed at least one of over and in the first layer.

In Example 23, the subject matter of any one of Examples 20 to 22 can optionally include that isolation structure includes or consists of a trench structure filled with a thermally insulating material.

In Example 24, the subject matter of Example 23 can optionally include that the trench structure completely laterally surrounds the second layer.

In Example 25, the subject matter of Example 24 can optionally include that the thermally insulating material physically connects the second layer to the first layer.

In Example 26, the subject matter of any one of Examples 20 to 22 can optionally include that the isolation structure includes or consists of thermally insulating material disposed over the first layer.

In Example 27, the subject matter of Example 26 can optionally include that the thermally insulating material completely laterally surrounds the second layer.

In Example 28, the subject matter of Example 27 can optionally include that the thermally insulating material physically connects the second layer to the first layer.

With reference to Examples 25 and 28, the thermally insulating material may physically contact the first layer and the second layer.

In Example 29, the subject matter of any one of Examples 23 to 28 can optionally include that the thermally insulating material includes or consists of an oxide.

In Example 30, the subject matter of Example 29 can optionally include that the oxide is silicon oxide ($SiO_2$).

In Example 31, the subject matter of any one of Examples 20 to 30 can optionally include that the first layer includes or consists of semiconductor material.

In Example 32, the subject matter of any one of Examples 20 to 31 can optionally include that the second layer includes or consists of semiconductor material.

In Example 33, the subject matter of Example 31 or 32 can optionally include that the semiconductor material is silicon.

In Example 34, the subject matter of any one of Examples 20 to 33 can optionally include that the light detecting structure is disposed in the first layer.

In Example 35, the subject matter of Example 34 can optionally include that the light detecting structure is disposed laterally next to the cavity structure.

In Example 36, the subject matter of any one of Examples 20 to 35 can optionally include a measurement circuit coupled to the light detecting structure to provide a signal representing measuring data from the light detecting structure.

In Example 37, the subject matter of Example 36 can optionally include an analog-digital converter connected to the measurement-circuit. The analog-digital converter may be configured to convert an analog measurement signal obtained from the light detecting structure to a digital measurement signal.

In Example 38, the subject matter of Example 37 can optionally include a digital signal processor connected to the analog-digital converter. The digital signal processor may be configured to provide an output-signal based on the digital measurement signal. The output signal representing a light intensity sensed by the light detecting structure.

In Example 39, the subject matter of Example 36 can optionally include an analog signal processor connected to the measurement-circuit. The analog signal processor may be configured to provide an output-signal based on an analog measurement signal obtained from the light detecting structure. The output signal representing a light intensity sensed by the light detecting structure.

In Example 40, the subject matter of any one of Examples 10 to 39 can optionally include that the spacer structure is arranged to provide the channel over the at least one heating structure. The heating structure is therefore arranged to directly heat the fluid flowing in the channel. The heating structure may have a surface that is exposed to an interior of the channel.

In Example 41, the subject matter of any one of Examples 10 to 40 can optionally include that the spacer structure is configured to provide the channel over the at least one light detecting structure. The light detecting structure is therefore arranged to receive light (e.g. only) from an interior of the channel. The light detecting structure may have a light blocking structure that prevents a detection of light that is not emitted from the light emitting structure.

In Example 42, the subject matter of any one of Examples 10 to 41 can optionally include that the spacer structure includes at least two sidewalls extending away from the first carrier to provide the channel between the at least two sidewalls. The channel may be configured substantially closed channel to provide a tubular passage for fluids, as for example a gas or a liquid.

In Example 43, the subject matter of any one of Examples 10 to 42 can optionally include that the light emitting structure is configured to emit light with a wavelength in the range from about 200 nm to about 1500 nm, e.g. in the range from about 300 nm to about 1300 nm.

In Example 44, the subject matter of any one of Examples 10 to 43 can optionally include that the light emitting structure includes at least one component of the following group of components: a light emitting diode, a laser diode, an organic light emitting diode. A light emitting diode may be formed in semiconductor material of the second carrier. Therefore, the semiconductor material of the second carrier may be doped to provide at least one junction, e.g. a p-n or an n-p junction.

In Example 45, the subject matter of any one of Examples 10 to 44 can optionally include that the light emitting structure includes at least one micro optical element. The at least one micro optical element may include at least one of the following group of optical elements: a mirror, a lens, an aperture, a filter, and the like.

In Example 46, the subject matter of any one of Examples 10 to 45 can optionally include that the light detecting structure includes at least one photo diode.

In Example 47, the subject matter of any one of Examples 10 to 46 can optionally include that the light detecting structure includes a first light detecting element disposed laterally next to the heating structure and a second light detecting element disposed laterally next to the heating structure, wherein the heating structure is arranged between the first detecting element and second light detecting element.

In Example 48, the subject matter of Example 47 can optionally include that the first detecting element is configured to receive unscattered light from the light emitting structure and that the second light detecting element is configured to receive scattered light from the light emitting structure.

In Example 49, the subject matter of Example 48 can optionally include that the light detecting structure includes an aperture disposed between the second light detecting element and the light emitting structure and configured to prevent a direct illumination of second light detecting element by the light emitting structure.

In Example 50, the subject matter of Example 48 or 49 can optionally include that the light detecting structure includes an aperture disposed between the first light detecting element and the light emitting structure and configured to allow substantially a direct illumination of second light detecting element by the light emitting structure.

Example 51 is a method for sensing a particle concentration or particle number in a fluid. The method includes: heating at least one heating structure of a particle sensor to provide a free convection flow of the fluid in a channel of the particle sensor, wherein the fluid includes particles; emitting light into the channel of the particle sensor by a light emitting structure of the particle sensor; detecting a first light intensity of the light emitted by the light emitting structure by a first light detecting structure of the particle sensor, wherein the first light detecting structure is arranged to receive light directly (i.e. unscattered light) from the light emitting structure; and detecting a second light intensity of the light emitted by the light emitting structure by a second light detecting structure of the particle sensor, wherein the second light detecting structure is arranged to receive only light from the light emitting structure that is scattered on particles in the channel.

In Example 52, the subject matter of Example 51 can optionally include determining a number of the particles or a concentration of the particles based on the detected first light intensity and second light intensity.

In Example 53, the subject matter of Example 51 or 52 can optionally include arranging the particle sensor so that the channel is arranged with an angle in the range from 0° to about 70° relative to a vertical direction.

Example 54 is a method for sensing a particle concentration or particle number in a fluid. The method including: heating a first heating structure of a first particle sensor to a first temperature thereby providing a first free convection flow of the fluid in a first channel of the first particle sensor; emitting light into the first channel of the first particle sensor by a first light emitting structure of the first particle sensor; detecting a first light intensity of the light emitted by the first light emitting structure by a first light detecting structure of the first particle sensor; heating a second heating structure of a second particle sensor to a second temperature thereby providing a second free convection flow of the fluid in a second channel of the second particle sensor; emitting light into the second channel of the second particle sensor by a second light emitting structure of the second particle sensor; detecting a second light intensity of the light emitted by the second light emitting structure by a second light detecting structure of the second particle sensor, wherein the first temperature is less than the second temperature.

Example 55 is a method for sensing a particle concentration or particle number in a fluid. The method including: heating a first heating structure of a first particle sensor thereby providing a first free convection flow of the fluid in a first channel of the first particle sensor; emitting light into the first channel of the first particle sensor by a first light emitting structure of the first particle sensor; detecting a first light intensity of the light emitted by the first light emitting structure by a first light detecting structure of the first particle sensor; heating a second heating structure of a second particle sensor thereby providing a second free convection flow of the fluid in a second channel of the second particle sensor; emitting light into the second channel of the second particle sensor by a second light emitting structure of the second particle sensor; detecting a second light intensity of the light emitted by the second light emitting structure by a second light detecting structure of the second particle sensor, wherein the first channel has a greater dimension than the second channel.

In Example 56, the subject matter of Example 54 or 55 can optionally include determining a number of the particles or a concentration of the particles based on the detected first light intensity and second light intensity.

In Example 57, the subject matter of Example 54 or 55 can optionally include determining a first number of the particles or a first concentration of the particles based on the detected first light intensity and determining a second number of the particles or a second concentration of the particles based on the detected second light intensity.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A particle sensor, comprising:
a first carrier, the first carrier comprising at least one heating structure, a light detecting device, and a first surface,
at least one spacer structure disposed over the first carrier,
a second carrier disposed over the at least one spacer structure, the second carrier comprising a light emitting device, and a first surface
wherein the first carrier, the second carrier and the at least one spacer structure are arranged to provide a channel for a fluid flow, wherein the first surface of the first carrier and the first surface of the second carrier face each other and are each exposed to the channel, wherein the light emitting device is configured to emit light into the channel and wherein the light detecting device is configured to detect light from the channel.

2. The particle sensor of claim 1,
wherein the channel has at least two openings defining a flow direction for a fluid from one of the at least two openings to another one of the at least two openings.

3. The particle sensor of claim 2,
wherein the channel is configured to have a length along the flow direction in the range from about 1 mm to about 10 mm.

4. The particle sensor of claim 2,
wherein the channel is configured to have a width perpendicular to the flow direction in the range from about 0.5 mm to about 2 mm.

5. The particle sensor of claim 4,
wherein the channel is configured to have a height perpendicular to the flow direction in the range from about 10 μm to about 500 μm.

6. The particle sensor of claim 2, further comprising:
at least two temperature sensors, wherein one of the at least two temperature sensors is configured to measure a temperature of the fluid at one of the at least two openings and wherein another one of the at least two temperature sensors is configured to measure a temperature of the fluid at another one of the at least two openings.

7. The particle sensor of claim 1, further comprising:
a driver circuit coupled to the at least one heating structure and configured to provide a heating current through the at least one heating structure.

8. The particle sensor of claim 7,
wherein the driver circuit is configured to control the heating current to provide a fluid flow with a flow velocity in the range from about 0.5 mm/s to about 5 mm/s.

9. The particle sensor of claim 1, further comprising:
a temperature sensor configured to measure a temperature of a fluid that flows in the channel.

10. The particle sensor of claim 1,
wherein the first and second carriers each comprise a semiconductor substrate.

11. The particle sensor of claim 10, wherein the light detecting device comprises a photodiode integrated in and/or over the first surface of the first carrier.

12. The particle sensor of claim 10, wherein the light emitting device comprises a diode integrated in and/or over the first surface of the second carrier.

13. A particle sensor, comprising:
a first carrier;
an isolation structure disposed at least one of over and in the first carrier;
a cavity structure disposed at least one of over and in the first carrier, the cavity structure comprising at least one cavity that is free of solid material;
a heating layer disposed over the cavity structure, wherein the isolation structure isolates the heating layer from the first carrier;
an electrode structure electrically contacting the heating layer to provide an electrical heating current through the heating layer;
a light detecting device disposed at least one of over and in the first carrier,
at least one spacer structure disposed over the first carrier,
a second carrier disposed over the at least one spacer structure, the second carrier comprising a light emitting device,
wherein the first carrier, the second carrier and the at least one spacer structure are arranged to provide a channel for a fluid flow, wherein the heating layer is arranged to heat a fluid in the channel, wherein the light emitting device is configured to emit light into the channel, and wherein the light detecting device is configured to detect light from the channel.

14. The particle sensor of claim 13, further comprising:
a driver circuit coupled to the electrode structure to provide a heating current through the heating layer.

15. The particle sensor of claim 13,
wherein the isolation structure comprises a trench structure filled with a thermally insulating material.

16. The particle sensor of claim 15;
wherein the trench structure completely laterally surrounds the heating layer and
wherein the thermally insulating material physically connects the heating layer to the first carrier.

17. The particle sensor of claim 13,
wherein the isolation structure comprises thermally insulating material disposed over the first carrier and wherein the thermally insulating material physically connects the heating layer to the first carrier.

18. The particle sensor of claim 13,
wherein the cavity structure is disposed between the first carrier and the heating layer.

19. The particle sensor of claim 13,
wherein the at least one cavity of the cavity structure is air-tightly sealed by the first carrier, the isolation structure, and the heating layer.

20. The particle sensor of claim 13,
wherein the at least one cavity of the cavity structure is air-tightly sealed and
wherein a vacuum is provided within the at least one cavity.

21. The particle sensor of claim 13,
wherein the light detecting device comprises at least one photo diode and wherein the light emitting device comprises at least one light emitting diode.

22. The particle sensor of claim 13,
wherein the first carrier comprises semiconductor material and wherein the heating layer comprises semiconductor material.

23. The particle sensor of claim 13,
wherein the isolation structure comprises an oxide.

* * * * *